(12) United States Patent
Misawa et al.

(10) Patent No.: US 7,195,915 B2
(45) Date of Patent: Mar. 27, 2007

(54) VECTORS FOR ANIMAL CELLS AND USE THEREOF

(75) Inventors: Elisa Misawa, Tokyo-to (JP); Hiroaki Yajima, Kanagawa-ken (JP); Keiji Kondo, Kanagawa-ken (JP)

(73) Assignee: Kirin Beer Kabushiki Kaisha, Tokyo-To (JP)

( * ) Notice: Subject to any disclaimer, the term of this patent is extended or adjusted under 35 U.S.C. 154(b) by 0 days.

(21) Appl. No.: 11/284,905

(22) Filed: Nov. 23, 2005

(65) Prior Publication Data

US 2006/0078992 A1    Apr. 13, 2006

Related U.S. Application Data

(62) Division of application No. 10/471,009, filed as application No. PCT/JP02/02201 on Mar. 8, 2002, now Pat. No. 7,064,194.

(30) Foreign Application Priority Data

Mar. 9, 2001    (JP) ................ 2001-66925

(51) Int. Cl.
*C12N 15/00* (2006.01)
*C12N 5/10* (2006.01)
*C12N 5/16* (2006.01)

(52) U.S. Cl. .............. 435/455; 435/325; 435/358

(58) Field of Classification Search .............. None
See application file for complete search history.

(56) References Cited

FOREIGN PATENT DOCUMENTS

WO    WO 93/02201    2/1993

OTHER PUBLICATIONS

Blitvich et al., "Molecular Cloning and Complete cDNA Sequence of the Ribosomal Proteins rpL34 and rpL44 from *Aedes Triseriatus* Mosquitoes", DNA Sequence, vol. 11(5), pp. 451-455, 2000.
Davies, M.S., Characterization of an mRNA encoding a human ribosomal protein homologous to the yeast L44 ribosomal protein. Gene, vol. 45, No. 2, pp. 183-191 (1986).
Del Pozo et al., "Cycloheximide resistance as a yeast cloning marker", Curr Genet (1991), pp. 353-358.
Jahn et al., "Sequence of the macronuclear DNA encoding large subunit ribosomal protein 29 (L29) in *Euplotes crassus* and cycloheximide sensitivity", Gene, 151 (1994), 231-235.
Kondo, K. et al., A transformation system for the yeast *Candida utilis*: use of a modified endogenous ribosomal protein gene as a drugresistant marker and ribosomal DNA as an integration target for vector DNA. J. Vacteriol., vol. 177, No. 24, pp. 7171-7177 (1995).
Mutoh et al., "Inducible Expression of a Gene Encoding an L41 Ribosomal Protein Responsible for the Cycloheximide-Resistant Phenotype in the Yeast *Candida maltosa*," 1995, J. Bacteriol., vol. 177, pp. 5383-5386.
Rhoads et al., "Emetine Resistance of Chinese Hamster Cells: Structures of Wild-Type and Mutant Ribosomal Protein S14 mRNAs," 1985, Mol. Cell. Biol., vol. 5, pp. 1655-1659.
Stevens et al., "Cycloheximide resistance conferred by novel mutations in ribosomal protein L41 of *Chlamydomonas reinhardtii*", Mol. Gen. Genet. (2001), 264: 790-795.

*Primary Examiner*—Scott D. Priebe
*Assistant Examiner*—Michael Burkhart
(74) *Attorney, Agent, or Firm*—Foley & Lardner LLP

(57) ABSTRACT

Protein synthesis inhibitor resistance genes (typified by a cycloheximide resistance gene) are capable of imparting resistance to a protein synthesis inhibitor (typified by cycloheximide) to animal cells sensitive to the inhibitor. The genes have a sequence mutated by substitution in a gene encoding a ribosome-constituting protein derived from an animal. The genes may be placed in recombinant vectors, including expression vectors containing the gene together with a foreign protein structural gene.

6 Claims, 13 Drawing Sheets

```
           ....|....|  ....|....|  ....|....|  ....|....|  ....|....|
               10          20          30          40          50
L36A       MVNVPKTRRT  FCKKCGKHQP  HKVTQYKKGK  DSLYAQGRRR  YDRKQSGYGG
L41        MVNVPKTRRT  YCKECRKHTQ  HKVTQYKAGK  ASLFAQGKRR  YDRKQSGYGG
                           |
                           KG

....|....|  ....|....|  ....|....|  ....|....|  ....|....|
               60          70          80          90          100
L36A       QTKPIFRKKA  KTTKKIVLRL  ECVEPNCRSK  RMLAIKRCKH  FELGGDKKRK
L41        QTKPVFHKKA  KTTKKVVLRL  ECV-V-CKTK  AQLALKRCKH  FELGGDKKQK
                                         Q
           ....|.
               106
L36A       GQVIQF
L41        GQALQF
```

FIG. 1

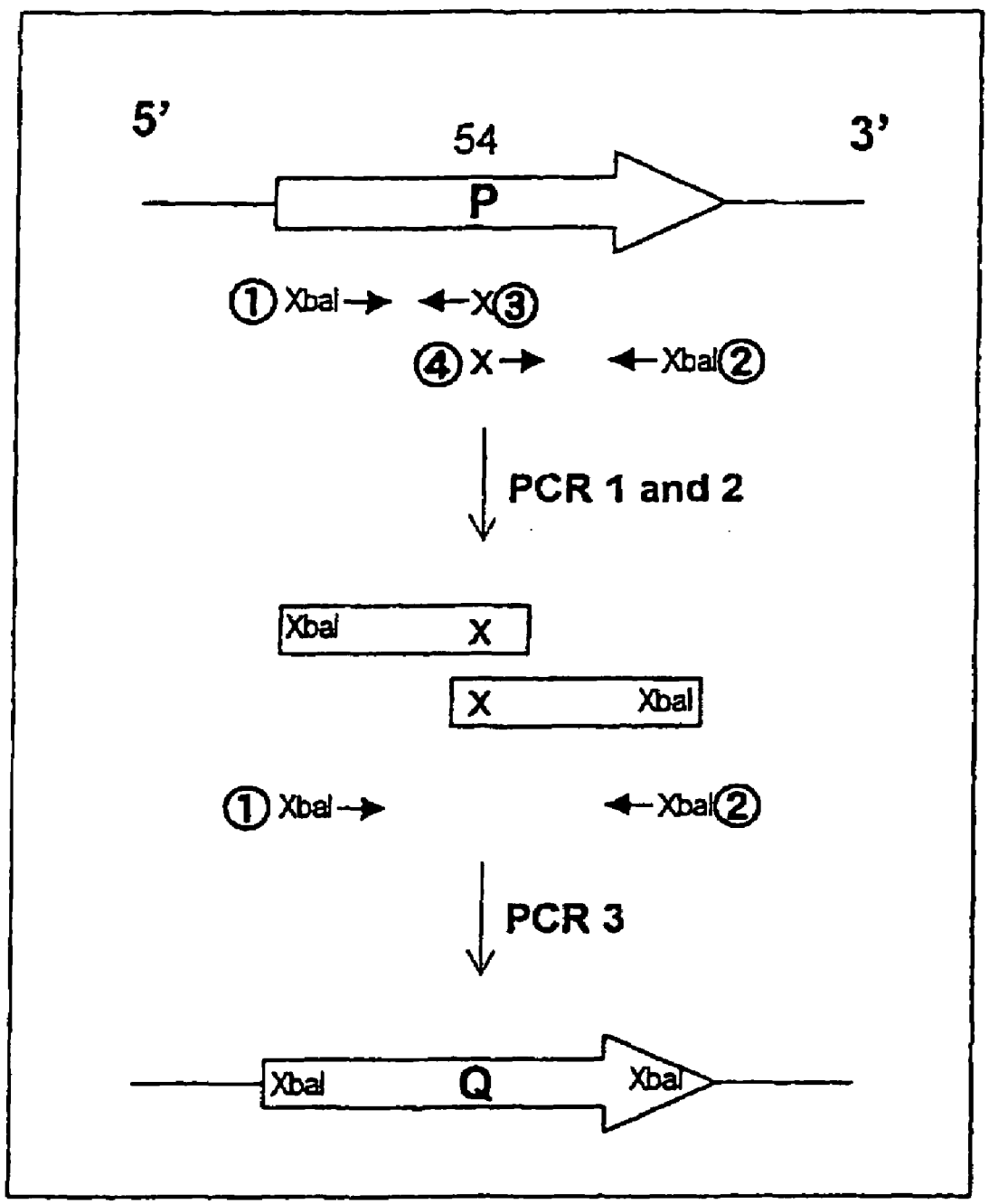
F I G. 2

| | | | | | | | | | | | | | | | |
|---|---|---|---|---|---|---|---|---|---|---|---|---|---|---|---|
| 1 | TCTAGA | | ATG | GTC | AAC | GTA | CCT | AAA | ACC | CGA | AGA | ACC | TTC | TGT AAG | 45 |
| | Xbal | | Met | Val | Asn | Val | Pro | Lys | Thr | Arg | Arg | Thr | Phe | Cys Lys | 13 |
| 46 | AAG | TGT | GGC | AAG | CAT | CAG | CCT | CAC | AAA | GTG | ACA | CAG | TAT | AAG AAG | 90 |
| 14 | Lys | Cys | Gly | Lys | His | Gln | Pro | His | Lys | Val | Thr | Gln | Tyr | Lys Lys | 28 |
| 91 | GGC | AAG | GAT | TCT | TTG | TAT | GCC | CAG | GGA | AGG | AGG | CGC | TAT | GAT CGG | 135 |
| 29 | Gly | Lys | Asp | Ser | Leu | Tyr | Ala | Gln | Gly | Arg | Arg | Arg | Tyr | Asp Arg | 43 |
| 136 | AAG | CAG | AGT | GGC | TAT | GGT | GGG | CAG | ACA | AAG | CAA | ATT | TTC | CGG AAG | 180 |
| 44 | Lys | Gln | Ser | Gly | Tyr | Gly | Gly | Gln | Thr | Lys | Gln | Ile | Phe | Arg Lys | 58 |
| 181 | AAG | GCT | AAG | ACC | ACA | AAG | AAG | ATT | GTG | CTA | AGG | CTG | GAA | TGT GTT | 225 |
| 59 | Lys | Ala | Lys | Thr | Thr | Lys | Lys | Ile | Val | Leu | Arg | Leu | Glu | Cys Val | 73 |
| 226 | GAG | CCT | AAC | TGC | AGA | TCC | AAG | AGG | ATG | CTG | GCC | ATT | AAG | AGA TGC | 270 |
| 74 | Glu | Pro | Asn | Cys | Arg | Ser | Lys | Arg | Met | Leu | Ala | Ile | Lys | Arg Cys | 88 |
| 271 | AAG | CAT | TTT | GAA | CTG | GGA | GGA | GAT | AAG | AAG | AGA | AAG | GGC | CAA GTG | 315 |
| 89 | Lys | His | Phe | Glu | Leu | Gly | Gly | Asp | Lys | Lys | Arg | Lys | Gly | Gln Val | 103 |
| 316 | ATC | CAG | TTC | TAA | TCTAGA | 333 | | | | | | | | | |
| 104 | Ile | Gln | Phe | End | Xbal | | | | | | | | | | |

FIG. 3

SEQUENCE LISTING

```
<160> NUMBER OF SEQ ID NOS: 17

<210> SEQ ID NO 1
<211> LENGTH: 333
<212> TYPE: DNA
<213> ORGANISM: Homo sapiens
<220> FEATURE:
<221> NAME/KEY: CDS
<222> LOCATION: (7)..(324)
<220> FEATURE:
<223> OTHER INFORMATION: ribosomal protein L36a gene

<400> SEQUENCE: 1 tctaga atg gtc aac gta cct aaa acc cga aga acc ttc tgt aag aag        48
       Met Val Asn Val Pro Lys Thr Arg Arg Thr Phe Cys Lys Lys
        1               5                  10 tgt ggc aag cat cag cct cac aaa gtg aca cag tat aag aag ggc aag       96
Cys Gly Lys His Gln Pro His Lys Val Thr Gln Tyr Lys Lys Gly Lys
 15                  20                  25                  30 gat tct ttg tat gcc cag gga agg agg cgc tat gat cgg aag cag agt      144
Asp Ser Leu Tyr Ala Gln Gly Arg Arg Arg Tyr Asp Arg Lys Gln Ser
                 35                  40                  45 ggc tat ggt ggg cag aca aag caa att ttc cgg aag aag gct aag acc      192
Gly Tyr Gly Gly Gln Thr Lys Gln Ile Phe Arg Lys Lys Ala Lys Thr
             50                  55                  60 aca aag aag att gtg cta agg ctg gaa tgt gtt gag cct aac tgc aga      240
Thr Lys Lys Ile Val Leu Arg Leu Glu Cys Val Glu Pro Asn Cys Arg
         65                  70                  75 tcc aag agg atg ctg gcc att aag aga tgc aag cat ttt gaa ctg gga      288
Ser Lys Arg Met Leu Ala Ile Lys Arg Cys Lys His Phe Glu Leu Gly
     80                  85                  90 gga gat aag aag aga aag ggc caa gtg atc cag ttc taatctaga            333
Gly Asp Lys Lys Arg Lys Gly Gln Val Ile Gln Phe
 95                 100                 105
```

<210> SEQ ID NO 2
<211> LENGTH: 333
<212> TYPE: DNA
<213> ORGANISM: Homo sapiens
<220> FEATURE:
<221> NAME/KEY: CDS
<222> LOCATION: (7)..(324)
<220> FEATURE:
<223> OTHER INFORMATION: ribisomal protein L44 gene

<400> SEQUENCE: 2

```
tctaga atg gtc aac gta cct aaa acc cga aga acc ttc tgt aag aag        48
       Met Val Asn Val Pro Lys Thr Arg Arg Thr Phe Cys Lys Lys
        1               5                  10 tgt ggc aag cat cag cct cac aaa gtg aca cag tat aag aag ggc aag        96
Cys Gly Lys His Gln Pro His Lys Val Thr Gln Tyr Lys Lys Gly Lys
 15                  20                  25                  30 gat tct ttg tat gcc cag gga aag agg cgc tat gat cgg aag cag agt       144
Asp Ser Leu Tyr Ala Gln Gly Lys Arg Arg Tyr Asp Arg Lys Gln Ser
                 35                  40                  45 ggc tat ggt ggg cag aca aag caa att ttc cgg aag aag gct aag acc       192
Gly Tyr Gly Gly Gln Thr Lys Gln Ile Phe Arg Lys Lys Ala Lys Thr
             50                  55                  60 aca aag aag att gtg cta agg ctg gaa tgt gtt gag cct aac tgc aga       240
Thr Lys Lys Ile Val Leu Arg Leu Glu Cys Val Glu Pro Asn Cys Arg
 65                  70                  75 tcc aag agg atg ctg gcc att aag aga tgc aag cat ttt gaa ctg gga       288
Ser Lys Arg Met Leu Ala Ile Lys Arg Cys Lys His Phe Glu Leu Gly
                 80                  85                  90 gga gat aag aag aga aag ggc caa gtg atc cag ttc taatctaga            333
Gly Asp Lys Lys Arg Lys Gly Gln Val Ile Gln Phe
             95                 100                 105
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
agaagtgtgg caagcatcag                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
ctcctcccag ttcaaaatgc                   20

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
gggtctagaa tggtcaacgt acctaaaac          29

```
<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccggaaaatt tgctttgtct gccca                                          25

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggcagacaa agcaaatttt ccgg                                           24

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggtctagat tagaactgga tcacttggc                                      29

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggttaccact cccactgact tcc                                            23

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcaacttcca gaccattggc                                                20

<210> SEQ ID NO 11
<211> LENGTH: 106
<212> TYPE: PRT
<213> ORGANISM: Homo sapiens

<400> SEQUENCE: 11

Met Val Asn Val Pro Lys Thr Arg Arg Thr Phe Cys Lys Lys Cys Gly
  1               5                  10                  15

Lys His Gln Pro His Lys Val Thr Gln Tyr Lys Lys Gly Lys Asp Ser
             20                  25                  30
```

```
Leu Tyr Ala Gln Gly Arg Arg Tyr Asp Arg Lys Gln Ser Gly Tyr
            35                  40                  45

Gly Gly Gln Thr Lys Gln Ile Phe Arg Lys Lys Ala Lys Thr Thr Lys
     50                  55                  60

Lys Ile Val Leu Arg Leu Glu Cys Val Glu Pro Asn Cys Arg Ser Lys
 65                  70                  75                  80

Arg Met Leu Ala Ile Lys Arg Cys Lys His Phe Glu Leu Gly Gly Asp
                85                  90                  95

Lys Lys Arg Lys Gly Gln Val Ile Gln Phe
             100                 105

<210> SEQ ID NO 12
<211> LENGTH: 106
<212> TYPE: PRT
<213> ORGANISM: Homo sapiens

<400> SEQUENCE: 12

Met Val Asn Val Pro Lys Thr Arg Arg Thr Phe Cys Lys Lys Cys Gly
 1               5                  10                  15

Lys His Gln Pro His Lys Val Thr Gln Tyr Lys Lys Gly Lys Asp Ser
             20                  25                  30

Leu Tyr Ala Gln Gly Lys Arg Arg Tyr Asp Arg Lys Gln Ser Gly Tyr
            35                  40                  45

Gly Gly Gln Thr Lys Gln Ile Phe Arg Lys Lys Ala Lys Thr Thr Lys
     50                  55                  60

Lys Ile Val Leu Arg Leu Glu Cys Val Glu Pro Asn Cys Arg Ser Lys
 65                  70                  75                  80

Arg Met Leu Ala Ile Lys Arg Cys Lys His Phe Glu Leu Gly Gly Asp
                85                  90                  95

Lys Lys Arg Lys Gly Gln Val Ile Gln Phe
             100                 105

<210> SEQ ID NO 13
<211> LENGTH: 106
<212> TYPE: PRT
<213> ORGANISM: Homo sapiens

<400> SEQUENCE: 13

Met Val Asn Val Pro Lys Thr Arg Arg Thr Phe Cys Lys Lys Cys Gly
 1               5                  10                  15

Lys His Gln Pro His Lys Val Thr Gln Tyr Lys Lys Gly Lys Asp Ser
             20                  25                  30

Leu Tyr Ala Gln Gly Arg Arg Tyr Asp Arg Lys Gln Ser Gly Tyr
            35                  40                  45

Gly Gly Gln Thr Lys Pro Ile Phe Arg Lys Lys Ala Lys Thr Thr Lys
     50                  55                  60

Lys Ile Val Leu Arg Leu Glu Cys Val Glu Pro Asn Cys Arg Ser Lys
 65                  70                  75                  80

Arg Met Leu Ala Ile Lys Arg Cys Lys His Phe Glu Leu Gly Gly Asp
                85                  90                  95

Lys Lys Arg Lys Gly Gln Val Ile Gln Phe
             100                 105

<210> SEQ ID NO 14
<211> LENGTH: 104
<212> TYPE: PRT
<213> ORGANISM: Candida utilis
```

```
<400> SEQUENCE: 14

Met Val Asn Val Pro Lys Thr Arg Arg Thr Tyr Cys Lys Glu Cys Arg
 1               5                  10                  15

Lys His Thr Gln His Lys Val Thr Gln Tyr Lys Ala Gly Lys Ala Ser
             20                  25                  30

Leu Phe Ala Gln Gly Lys Arg Arg Tyr Asp Arg Lys Gln Ser Gly Tyr
         35                  40                  45

Gly Gly Gln Thr Lys Pro Val Phe His Lys Lys Ala Lys Thr Thr Lys
     50                  55                  60

Lys Val Val Leu Arg Leu Glu Cys Val Val Cys Lys Thr Lys Ala Gln
 65                  70                  75                  80

Leu Ala Leu Lys Arg Cys Lys His Phe Glu Leu Gly Gly Asp Lys Lys
             85                  90                  95

Gln Lys Gly Gln Ala Leu Gln Phe
            100

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Syntheic
      linker sequence

<400> SEQUENCE: 15
cccggatccg gg                                                           12

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atgggtcaga aggattccta                                                   20

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tccatgtcgt cccagtt                                                      17
```

VECTORS FOR ANIMAL CELLS AND USE THEREOF

This application is a Divisional of U.S. application Ser. No. 10/471,009, filed Sep. 8, 2003, now U.S. Pat. No. 7,064,194, issued Jun. 20, 2006, which is a National Stage application of PCT/JP02/02201, filed Mar. 8, 2002, which claims priority from Japanese patent application JP 2001-66925, filed Mar. 9, 2001. The entire contents of each of the aforementioned applications are incorporated herein by reference.

TECHNICAL FIELD

The present invention relates to recombinant expression vectors for producing useful substances in animal cells, and to a process for producing proteins and the like by using the expression vectors, particularly to a technique for selecting cells, into which a gene has been stably transferred, by using a novel drug resistant gene as a selection marker, and to a technique for efficiently obtaining cells in which a gene is highly expressed.

BACKGROUND ART

<Production Techniques of Recombinant Proteins>

It has become possible to produce a variety of useful proteins including the ones occurring in an extremely small amount in an organism or having too low stability to be purified by the evolution of the recombinant expression techniques of a gene. The use of such techniques has realized not only the practical use of many recombinant proteins as pharmaceuticals or industrial enzymes, but also the elucidation of the stereostructures of proteins or the analysis of the interactions between proteins, and thus the comprehension of life has steeply proceeded. Furthermore, it has been possible to obtain useful genes by the steep proceeding of the genome studies on many biological species including human and the development of bioinformatics and PCR technologies. Therefore, unlike the conventional situations in which the cloning of genes has often been the rate determining factor of the studies, a great deal of time has now become required for developing the stable expression of a cloned gene, that is to say, the process for producing a protein encoded by the gene and in a large amount.

The hosts used for the production of recombinant proteins include *Escherichia coli*, yeast, cells derived from insects and mammals, but universal hosts for producing proteins which satisfy all of the needs have not yet been developed. Thus, trial and error must be carried out even now for the construction of production systems at every intended protein. By way of example, although *Escherichia coli* is the expression system used most popularly, it is at issue in the production of proteins having activities that the proteins produced often form insoluble inclusion bodies and post-translational modification such as glycosylation scarcely occurs distinct from eukaryotes. In addition, expression systems, in which eukaryotes such as yeasts or fungi are used as a host, are also used, but these systems are not always effective on all of the proteins and often difficult to conduct the expression of the activities or the complex post-translational modification of animal-derived proteins having complex structures. Furthermore, there has recently been often used an expression system with baculovirus and insect cells as a host cell. This system has many advantages in that the protein produced has been subjected to post-translational modifications such as phosphorylation and glycosylation and thus can be expressed with maintaining the original physiological activities, but the sugar chain structure of the secreted protein is different from that of the cells derived from mammals, so that problems such as the antigenicity of the recombinant proteins will be caused in pharmaceutical applications.

On the other hand, it is better to select an expression system with an organism related to the one from which a target protein is derived in order to produce the protein in the same state as in vivo, that is to say, in the same state in relation to the stereostructure of the protein maintained in an organism and the post-translational modifications such as phosphorylation, glycosylation and truncation. Therefore, an expression system having the cells derived from mammals as a host has been predominantly used in the expression of a protein which is derived from animals, in case that the post-translational modifications such as glycosylation to maintain the activity of the protein are required, the protein has a complicated structure, or the functions of the protein have not been identified. The expression system with animal cells is advantageous in that the protein can be subjected to precise post-translational modification, and thus proper folding can be expected for exerting its activities. Therefore, this is predicated the most appropriate system for the purpose of the biochemical analysis and functional analysis of proteins derived from animals.

Expression is classified into two types of the transient expression method in which a gene is expressed transiently and the stable expression method in which cells constantly expressing a gene are made. In the transient expression method, the transferred gene is transcribed and translated in the cells, and the expression of a protein is observed after several hours from the transfer and reaches its peak after two or three days. A method for amplifying the number of copies of a plasmid containing ori of SV40 by transferring the plasmid into cells such as COS cells in which the SV40 large T antigen gene is expressed is employed in order to increase the production amount of the protein, but it requires the transfer of the plasmid into the cells every time and thus the amount of the protein produced by this method is limited. On the other hand, when it is necessary to conduct the analysis with the cells in which the target protein has been constantly expressed or to produce the target protein in a certain amount, the stable expression method in which the transferred gene is inserted into the chromosome of the cells is selected. If a recombinant cell line having a high productivity of protein of interest has been established at all, all of the cells has expressed the target gene, so that a variety of analysis can be performed and culture in a large scale can also be conducted in order to produce a homogeneous recombinant protein. However, since the amount of gene expression largely varies among the recombinant cell lines due to the copies of the gene inserted into the chromosome of the cell or the position of the chromosome into which the gene has been inserted, a cell line having a high expression amount which can be used for the analysis or production must be selected. Most of the transformed cell clones, however, have extremely low expression amounts, and thus the selection of the high expression clone requires time-consuming and laborious operations.

As described above, in any cases of the production of a protein in either of the expression forms, various ideas have been managed to solve the problem that the production amounts of proteins in animal cells remain generally in lower levels as compared with those in the other recombinant expression host systems.

<Increase of the Expression Level of a Gene>

The expression level of an eukaryotic gene transferred into animal cells are regulated by various factors such as a DNA sequence which acts cis on the expression of the gene or the transcriptional regulatory factor which acts trans on the DNA sequence, the copy number of the gene, the insertion site of the transferred gene in chromosome, and the stability of mRNA (Dillon and Grosveld, Trends Genet., 9:134, 1993). The regulatory system has hitherto been analyzed from many aspects, and plasmid vectors for obtaining cell strains in which a gene is highly expressed have been developed on the basis of these results (Makrides S. C.; 1999). Typical information is now described below.

The cis-acting factors participating in the regulation of gene expression are DNA sequences, of which the typical ones includes promoter sequence and enhancer sequence. It has been examined thoroughly that a variety of transcriptional regulatory proteins which regulate transcription act as trans-acting factors on either sequence. The promoter sequence is adjacent to the upstream of the gene, and contains an essential region to basic transcription. The enhancer sequence may be present in a place apart from the gene or in an intron, and the orientation of the sequence is not fixed. Also, the enhancer sequence may often regulate the expression of a tissue-specific gene. The activities of promoters and enhancers can be generally detected for example by the transient gene transfer experiment. In order to highly express a foreign gene, it is important to arrange and utilize a potent promoter and an enhancer sequence effectively. The potent promoter sequence is often in close vicinity to the enhancer sequence, and includes for example SV40 early promoter, adenovirus major late promoter, mouse metallothionein I promoter, Raus sarcoma virus long terminal repeat and human cytomegalovirus (CMV) promoter.

In addition to the promoters and the enhancers, there are also cis-functional regulatory sequences for gene expression. These sequences are referred to as locus control region (LCR; Grosveld F., Cell 51:975, 1987), matrix attachment region (MAR; Phi-Van, Mol Cell Biol 10:2302, 1980), scaffold attachment region (SAR; Gasser, Trends Genet 3:16, 1987), or insulator element (Kellum, Cell 64:941, 1991), and are believed to act on the chromatin structure of chromosome. These regions have a function similar to the enhancer in view of point that these regions may function even if apart from the gene, but are distinguished from the enhancer sequences in that these regions can be detected only by the experiment of stably transferring a foreign gene into chromosome. Among these sequences, LCR is distinct from the enhancers in that it has functions depending on the site and orientation to the gene. Furthermore, the sequences called A box or T box and the topoisomerase II recognition sequence which are characteristically present in LCR and SAR are specific sequences which have not been found in the enhancer sequences or the promoter sequences (Klehr D., Biochemistry 30:1264, 1991).

HIRPE (Hot spot of Increased Recombinant Protein Expression) is a characteristic 5 kb DNA fragment which contains a sequence similar to MAR and an AT-enriched sequence, and is cloned from CHO cells in which a foreign gene is highly expressed (Koduri, K., Thammana, P., Patent No. WO 00/17337). It has been shown that the transformation of the CHO cells with an expression plasmid containing the DNA fragment linked with a foreign gene results in insertion of the plasmid into the particular site of chromosome and the increase of the expression level to several times. In addition, the expression augmenting sequence element (EASE; Morris, A. E., Patent No. WO97/25420) is also a factor discovered in CHO cells and is believed to have an effect of increasing the expression level of a foreign gene stably inserted into chromosome to several times. The activity is observed in a 14.5 kb DNA fragment cloned from the cells in which a foreign gene is highly expressed. No ORF which encodes regulatory factors is contained in the DNA fragment, and thus the effect of increasing the expression amount of the gene is thought due to the action of EASE, after having been inserted stably into chromosome, on a promoter or a enhancer sequence. Either method is a gene expression augmentation method with a certain specific DNA fragment, and thus these methods cannot be applied to the expression of the other foreign genes unless these DNA fragments are used.

Increased expression of a foreign gene can also be established by increasing the copy number of the gene in host cells. One of the methods for increasing the copy number of a foreign gene in transformed cells comprises co-transfecting the cells with a plasmid containing a selective marker gene and a large excessive amount of plasmid containing a foreign gene and no selective marker gene. According to this method, it is possible to obtain stably transfected cells in which a number of the foreign genes have been inserted into the chromosome (Kaufman, Meth. Enzymol., 185:537, 1990). However, since almost of the clones obtained by the transfection according to this method have only a few copies of the foreign gene, clones in which many copies of the foreign gene have been inserted must be screened, and thus time-consuming and laborious operations are required.

Another method for increasing the copy number of a foreign gene comprises gene amplification in the stably transfected cells which have been once selected. It is believed that the gene amplification naturally occurs in animal cells notwithstanding in a low frequency (Schimke R T, J Biol Chem, 1988, 263, 5989–92). There has been extensively employed a technique in which the foreign gene has preliminarily been transfected together with a gene which can be amplified into the host cells by taking advantage of the fact that the gene amplification is induced by exposing the cells to an appropriate selection pressure, the concentration of a selection agent is continuously increased, and thus the foreign gene is amplified together with the marker gene.

The marker gene generally used in this operation is a dhfr gene which encodes an enzyme dihydrofolate reductase, and the host cell which can be used is the CHO cell defective in dhfr activity. The gene is amplified by gradually increasing the concentration of the dhfr inhibitor methotrexate (MTX), and the target foreign gene in the vicinity thereof is also expected for amplification at the same time (Mammalian Cell Biotechnology, Ed. Butler, M. IRL Press, P 79). Furthermore, it has been described that the foreign gene can be amplified to the number of copies of 2000 by increasing the MTX concentration in three steps (Bebbington, C. and Hentschel, C., Trends Biotechnol., 3., 314 1985). However, this method has the problems that it is time-consuming and can be applied only to dhfr gene deficient cells. In addition, the agent for selection is expensive, and thus it is not preferred to add the agent in the large-scale culture of recombinant animal cells. Furthermore, it has been also indicated that the gene once amplified by this method is unstable and tends to be deleted under the condition of the non-addition of the agent ("Gene", Ver. 6, Translated by Tsuguhiko Kikuchi, P 845–848, Tokyo Kagaku Dojin).

<Establishment of Stable Cell Lines in Which Genes are Highly Expressed>

A selective marker gene is required for selecting the animal cells into which a foreign gene has been stably transferred. Various kinds of marker genes are used for selection and are classified largely into two groups. One of the groups includes genes of, for example, hypoxanthine-guanine phosphoribosyl transferase (HGPRT), thymidine kinase (TK), dihydrofolate reductase (DHFR), and adenine phosphoribosyl transferase (APRT), and only the cells deficient in the enzymatic activity corresponding to each of the genes may be used as the host. Since auxotrophy in such cells deficient in these enzymatic activities will be recovered by transferring the corresponding genes, it is possible to select the cell strains into which a foreign gene has been transferred. Another group is a gene group for conferring resistance to antibiotics and drugs which inhibit the growth of the cells. Specifically, it includes, for example, mutated DHFR for conferring resistance to methotrexate, xanthine-guanine phosphoribosyl transferase (gpt) for giving resistance to xanthine, and the transposon Tn5-derived aminoglycoside 3'-phosphotransferanse (neo) for giving resistance to drugs such as geneticin (G418), gentamycin, kanamycin, and neomycin. There have recently been developed also the genes for affording resistance to zeocin or hygromycin. These genes may be used as selective marker genes for all of the animal cells.

Cycloheximide (CYH) is a protein synthesis inhibitor, and an application example with the CYH resistant gene as a selective marker includes an example with yeast. It has been elucidated in yeasts that CYH acts on the L41 protein, the sub-unit of ribosomal protein, to inhibit the biosynthesis of the protein and become sensitive to CYH when the amino acid at the position 56 of the protein is proline while non-sensitive to CYH when the amino acid is glutamine (Kawai S. 1992, J. Bacteriol., 174, 254–262). Based on this information, it has been demonstrated that when the gene of the L41 protein is cloned from CYH sensitive yeasts such as *Candida utilis* and *Phaffia rhodozyma* and mutation by substitution is transferred to construct a gene of the L41-Q type, which is then transferred into the original yeasts, these yeasts become resistant to CYH (Kondo K., 1995, J. Bacteriol., 177, 24, 7171–7177; Kim I.-G., 1998, Appl. Environ. Microbiol., 64, 5, 1947–1949). However, there have been described no applications to higher eucaryotes such as animal cells.

Foreign gene transferring vectors into animal cells generally possess either one or both of these marker genes, and vectors into which a green fluorescent protein (GFP) has been contained are also used in order to select a high expressing strain more easily.

While clones in which the desired protein is highly expressed must be selected from many transfected cells obtained with the above described selective marker genes, a foreign gene in most of the transfected cells is generally expressed in an extremely low level and is screened with an extreme difficulty.

Therefore, there have been described several methods of directly selecting high-expression transformed cells. One of the methods comprises co-transfecting cells with a foreign gene and a dhfr gene, directly culturing the cells in a culture medium containing Mtx in a high concentration, and thus selecting the transduced cells in which dhfr is expressed in a high level. Many of the cells selected by this method express a foreign gene in a high level (Page M J, Sydenham M A, Biotechnology 9, 1991, 64–68). However, high-expression cells obtained directly by single step using a culture medium containing a selecting agent in a high concentration are inferior in growth and stability and thus inappropriate to the use for the production of proteins for a long period of time. Furthermore, among the recombinant cells obtained by the direct selection with Mtx, there may be preferentially selected cells which contain dhfr enzyme of which the sensitivity to Mtx have been changed or are hardly affected by Mtx.

The second method comprising expressing a gene, which encodes the desired protein, together with a selective marker gene by using one promoter and thus obtaining efficiently high-expression cells has also been used. In this method, a vector which is constructed to express mRNA consisting of the foreign gene at the 5'-side and the selective marker gene at the 3'-side is used. It is generally expected that since the translational efficiency of the gene at the 3'-terminus of a polycistonic mRNA is bad, the polycistonic mRNA is expressed in a high level in transducing cells selected, and the desired protein is expressed in a high level (Kaufman R J, Murtha P, Davies M V EMBO J, 6:187 1987). However, when the translational efficiency of the selective marker at the 3'-side is largely affected depending on the genes at the 5'-side or the expression of the selective marker gene at the 3'-side remains in an extremely low level, risks may happen that the transformed clone is not selected or a cell having an increased translational efficiency of the selective marker gene due to the partial deletion of the gene at the 5'-side is selected. Internal ribosome entry site (IRES) is a sequence discovered in, e.g. virus derived RNA, and has been confirmed to promote the binding of ribosome to mRNA and the initiation of translation (Kaufman R. J., Nucleic Acid Res 19:4485, 1991). It is possible to enhance the translational efficiency of the gene at the 3'-side on the polycistonic mRNA by taking advantage of this property, and vectors in which the high-expression cells are selected relatively easily have been developed with IRES.

As the third method, there is also mentioned a method in which the expression of the selective marker gene is artificially lowered for expecting the increase of the expression of the gene transferred into the transfected cell at the same time. For instance, an intron is arranged at the 5'-side of a gene in which the desired protein is encoded, and the selective marker gene is arranged within the intron. Thus, only the mRNA with the complete length which is present in a low frequency and will not be spliced produces selective marker proteins. It has been shown that the transcript of a gene containing the selective marker gene in the intron is expressed in a high level in such transduced strains selected by the plasmids, and thus the desired protein is expressed in a high level (Clorley, Craig W., WO 96/04391). Furthermore, there has been also reported a method for expressing a foreign gene in a high level in a selected transducing strain by diminishing the expression of a selective marker gene by modifying the DNA sequence around the translation initiating codon of the selective marker gene and lowering the translational efficiency of the gene (Reff Mitchell E. WO 98/41645).

DISCLOSURE OF THE INVENTION

As described above, in the expression system in which animal cells are employed as a host, the expressed protein can be expected to conduct folding proper for exerting its activities by precise post-translational modifications, and thus the system is the most appropriate for examining the functions of genes derived from human and the other animals and for producing a large amount of proteins encoded by the genes. However, the system has a serious defect of low productivity of protein as compared with the recombinant production systems with the other hosts. Therefore, it is necessary to screen high-expression clones from many clones into which DNA has been stably transfected in order to establish a high expression cell line. Even if a stably transfected cell in which the desired protein is expressed in a comparatively high level has been cloned, it is often necessary to conduct the laborious and time-consuming amplification operation of the transfected genes in order to produce the protein. From the above described reasons, there are desired further improvements in gene expression systems with animal cells including the development of techniques which enable the efficient selection of transformed animal cells in which a gene is expressed in a high level, the development of the gene stabilization technique in the obtained cells in which a gene is highly expressed, and the development of convenient gene amplification techniques.

The object of the present invention is to solve the above described problems, particularly to provide a novel vector containing a selective marker gene and enabling the high frequency of the selection of the recombinant cell in which a foreign gene is highly expressed, a method for efficiently selecting the high-expression strains with the vector, and a technique for producing proteins which enable the production of the desired proteins in a high level.

The present inventors have developed a gene coding for a mutant ribosome subunit constituting protein as a novel selective marker gene for animal cells, and demonstrated that the transduction of the gene confers the resistance to cycloheximide, a protein synthesis inhibitor, on the animal cells. In addition, the present inventors have also demonstrated in cycloheximide resistant animal cells which have been selected with the expression vector containing the gene that (i) a number of transformed cells are obtained in which the foreign gene is expressed in an extremely high level as compared with stably transfected cells selected with the pharmaceutical resistant genes which have hitherto been used, (ii) proteins coded by the foreign gene may be intracellular proteins or secretory proteins, and the above described trend will not be changed, and (iii) the high expression is stably maintained after sub-culture of the cells under the culturing condition in the absence of cycloheximide. Furthermore, the present inventors have also demonstrated, from the fact that no correlation is found between the copy number of the introduced gene and the expressivity, that the high expression of a gene may be caused by the increased frequencies of the foreign gene inserted in the high-expression site on the chromosome of the host cells by using the selective marker.

As described above, the present inventors have found the fact that a technique for efficiently selecting within a short time the cells in which a foreign gene is highly expressed can be established by transducing the foreign gene in the form of an expression plasmid with a new drug resistant gene as a selective marker into animal cells. On the basis of this information, we have accomplished the present invention.

In other words, the present invention relates to the following drug resistant genes, expression vectors, a process for screening the cells in which the gene is expressed in a high level, transformed cells, and a process for producing a recombinant protein.

(1) A drug resistant gene (protein synthesis inhibitor resistance gene) capable of imparting the resistance to a protein synthesis inhibitor to animal cells sensitive to the inhibitor and having a sequence mutated by substitution with a gene encoding a ribosome-constituting protein originating in an animal.

Typically, it is the protein synthesis inhibitor resistance gene (cycloheximide resistant gene) capable of imparting the resistance to cycloheximide to animal cells sensitive to cycloheximide and having a sequence mutated by substitution with a gene encoding the animal-derived ribosome-constituting protein L36a or a homologous protein thereof.

Another preferred embodiment is the cycloheximide resistant gene capable of imparting the resistance to cycloheximide to animal cells sensitive to cycloheximide and encoding an amino acid sequence represented by SEQ ID Nos. 1 or 2, or the amino acid sequence in which one or several amino acids have been subjected to substitution, deletion, insertion or addition.

(2) A recombinant vector containing such a protein synthesis inhibitor resistance gene as described above.

(3) An expression vector containing the above described gene together with a foreign protein structural gene.

(4) A method of selecting an animal cell strain resistant to a protein synthesis inhibitor into which the expression vector has been transduced.

Specifically, a method of selecting an animal cell strain resistant to a protein synthesis inhibitor, in which the expression vector is transduced into animal cells sensitive to the protein synthesis inhibitor, the cells are cultured and then the target cell strain is selected by using the protein synthesis inhibitor resistance gene as a selection marker.

(5) A transformed cell comprising the animal cells in which the expression vector is contained.

(6) A process for producing a protein in which the transformed cells are cultured and an expressed foreign protein is harvested from the culture.

BRIEF DESCRIPTION OF THE DRAWINGS

FIG. 1 illustrates the amino acid sequence of the human ribosomal protein L36a (GI 4506651) (SEQ ID NO:13) compared with that of the yeast *Candida utilis* ribosomal protein L41 (GI1255906) (SEQ ID NO:14).

Figure 4:
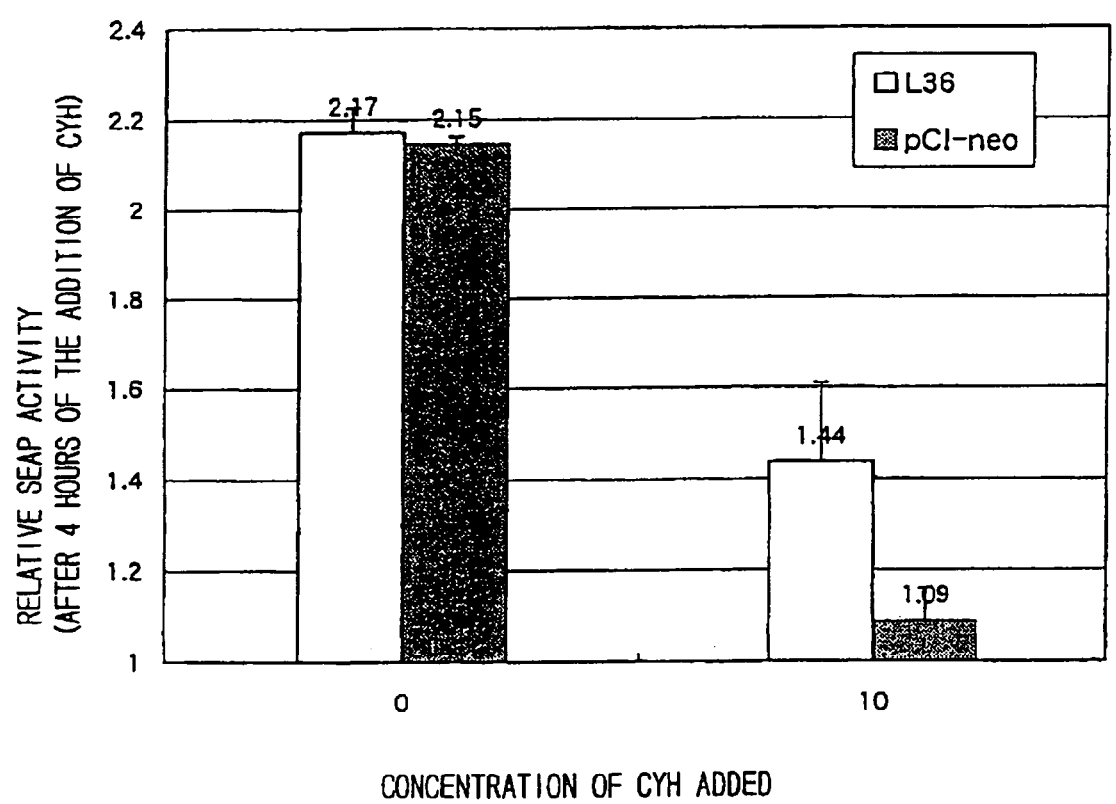

Substitution of the amino acid proline (enclosed with a square) at the position 54 in the human L36a protein (or at the position 56 in the yeast L41 protein) by glutamine produces cycloheximide resistant proteins, respectively.

FIG. 2 illustrates the method of constructing the cycloheximide resistant gene by the two-step PCR.

First, PCR was carried out on the combination of primers 1 and 3 and on the combination of primers 4 and 2 with the L36a gene as a template. A part of the nucleotide sequence of the primer 3 and 4 was different from that of the template in order to substitute the amino acid proline at the position 54 by glutamine. PCR carried out again on the combination of primers 1 and 2 with the mixture of the two PCR products thus obtained as a template resulted in the addition of the restriction enzyme XbaI recognition site to both termini, and a CYH resistant L36a gene in which the amino acid proline at the position 54 has been substituted by glutamine can be obtained.

FIG. 3 illustrates the DNA sequence of the CYH resistant L36a gene (L36a-CYH$^R$ gene) (SEQ ID NO:1) and the amino acid sequence of a polypeptide encoded by the gene (SEQ ID NO:11).

Glutamine at the position 54 into which amino acid mutation has been introduced was enclosed with square.

FIG. 4 illustrates the resistance to cycloheximide imparted by L36a-CYH$^R$ gene.

The plasmid pCI-neo-L36 containing L36a-CYH$^R$ gene was co-transfected together with the pSEAP2-control containing secretory alkaline phosphatase SEAP into the CHO cells, the culture medium was changed into the fresh one after 24 hours, and a portion of the supernatant was collected after 4 and 8 hours, respectively, to determine the SEAP activity. The activity after 8 hours was shown as compared with the activity after 4 hours as 1.

Figure 5:
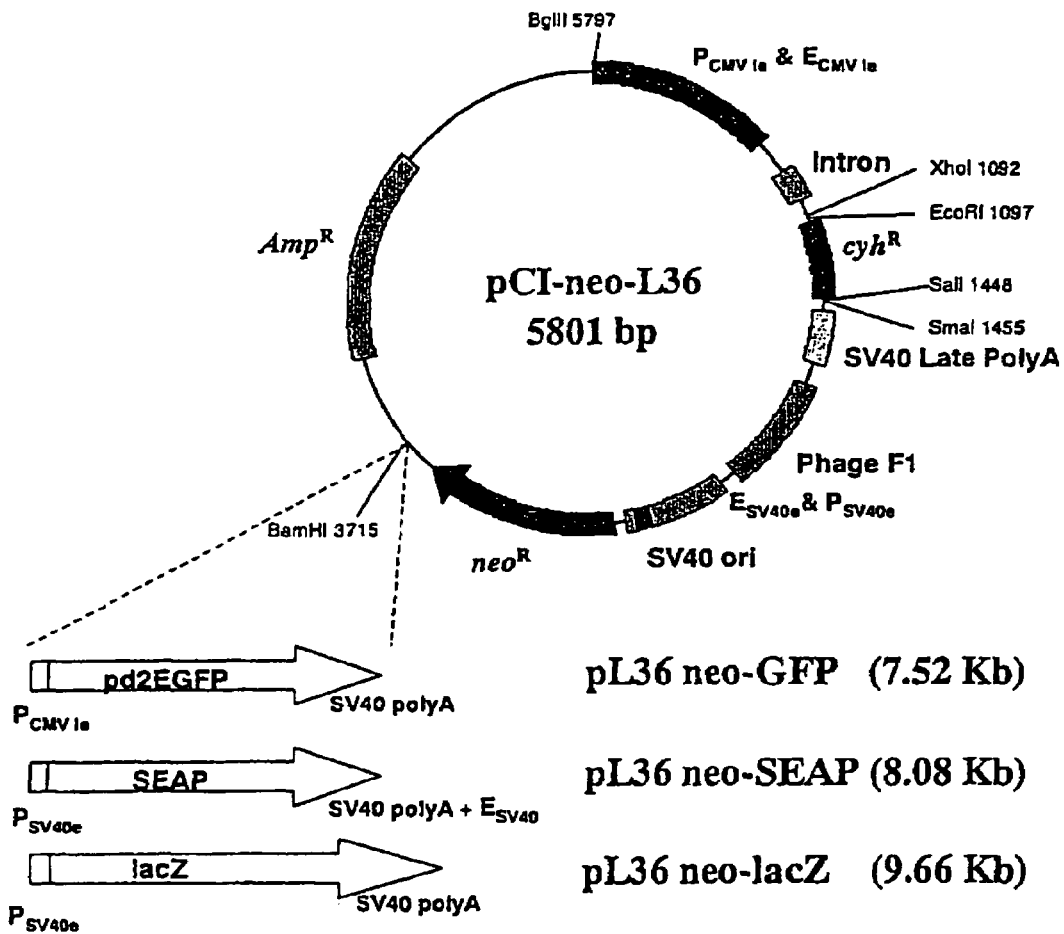

FIG. 5 illustrates the structures of various plasmid.

Figure 6:
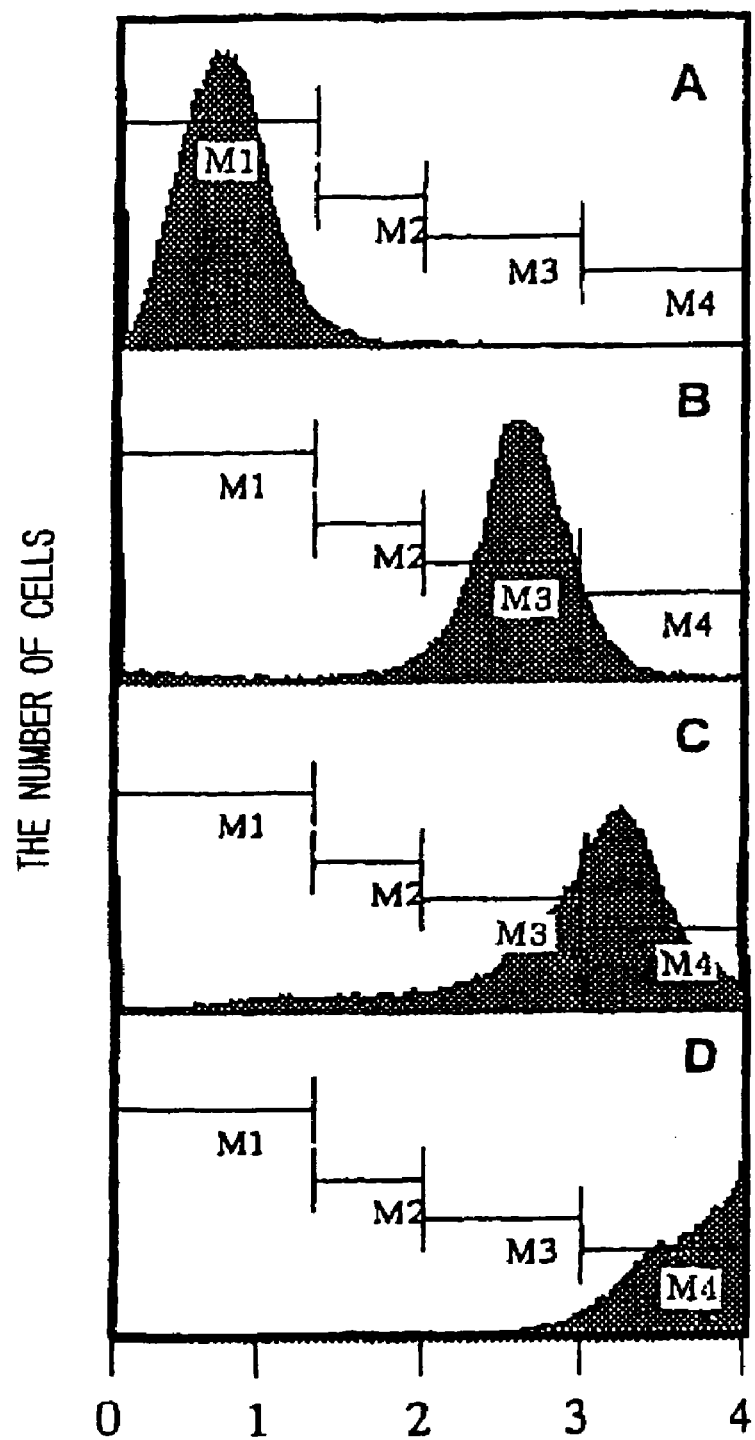

FIG. 6 illustrates the method of analyzing the GFP expressions by flow cytometry.

Cell numbers were plotted on the ordinate, and fluorescence intensities due to the GFP expression were logarithmically plotted on the abscissa. The fluorescence intensities were classified into four regions in the increasing order of M1–M4, and the cells included in the region M1 were regarded as the group of cells in which GFP is not expressed, while the cells included in the regions M3 and M4 were regarded as the group of cells in which the expression of GFP is positive.

Figure 7:
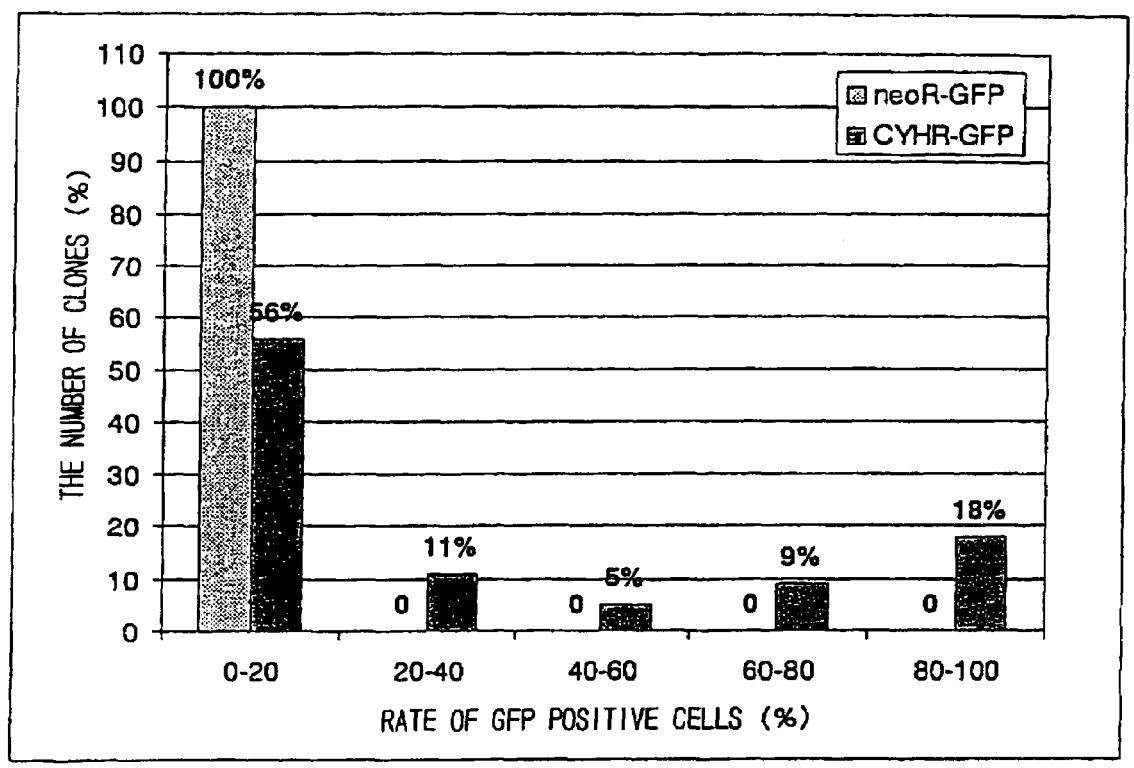

FIG. 7 illustrates the GFP expressions of the isolated CYH resistant and G418 resistant clones.

The CYH resistant 44 clones obtained by transfecting pL36a-neo-GFP and the 46 G418 resistant clones obtained by transfecting pd2EGFP-N1 were analyzed.

Figure 8:
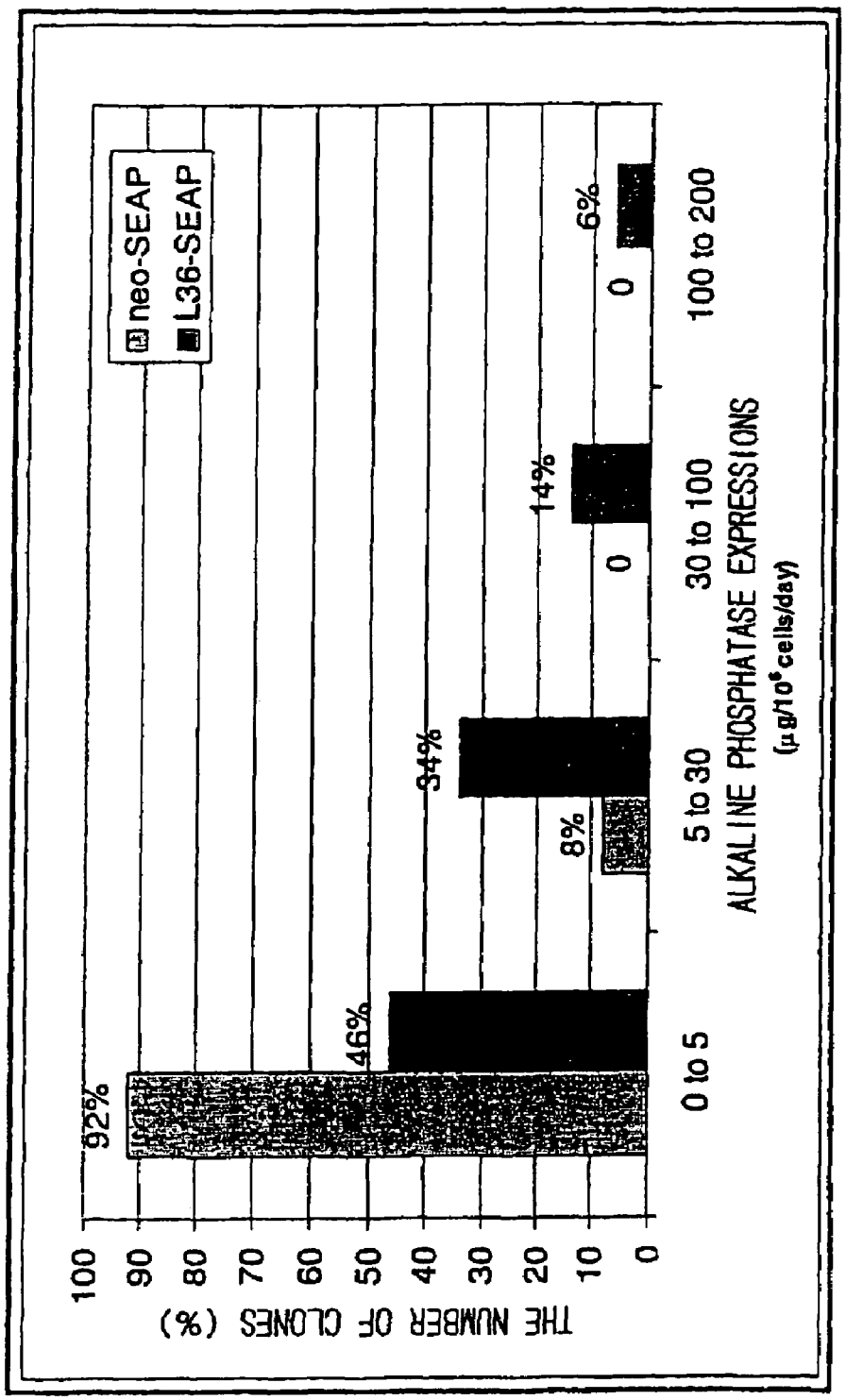

FIG. 8 illustrates the distributions of alkaline phosphatase expressions in the isolated CYH resistant and G418 resistant clones.

The 50 CYH resistant clones obtained by transfecting pL36a-neo-SEAP and the 50 G418 resistant clones obtained by transfecting pNeo-SEAP were analyzed.

Figure 9:
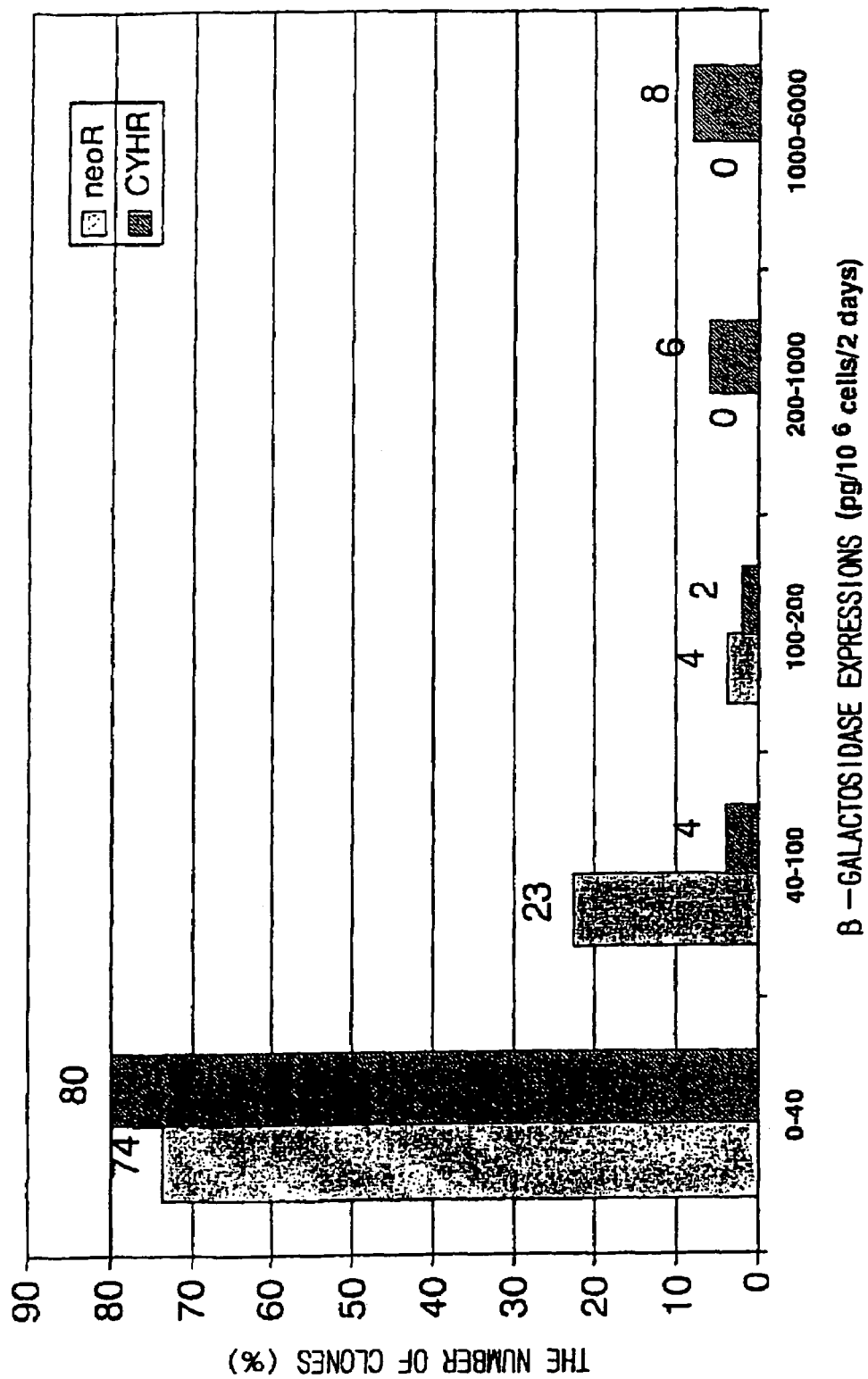

FIG. 9 illustrates the distributions of β-galactosidase expressions in the isolated CYH resistant and G418 resistant clones.

The 50 CYH resistant clones obtained by transfecting pL36a-neo-lacZ and the 50 G418 resistant clones obtained by transfecting pNeo-lacZ were analyzed.

Figure 10:
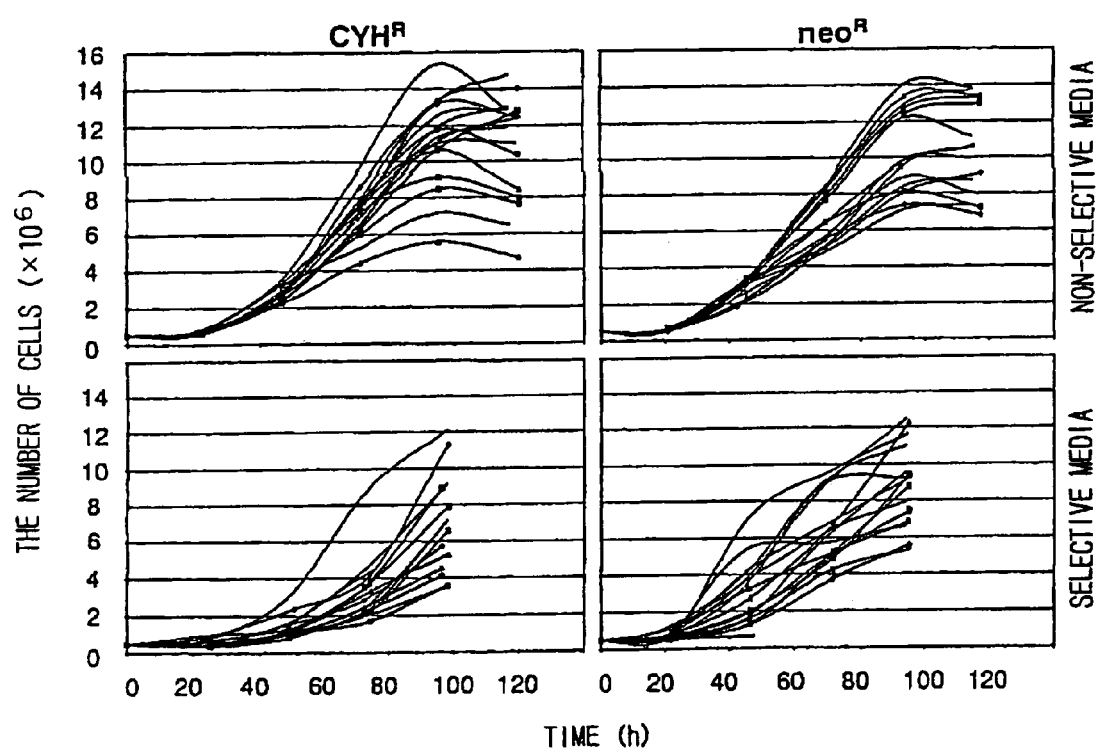

FIG. 10 illustrates the growth curves of the CYH resistant alkaline phosphatase expression clones and the G418 resistant alkaline phosphatase expression clones.

Each 15 clones were randomly selected from the CYH resistant and the G418 resistant clones in which the SEAP gene has been stably transfected, respectively and cultured in selective media (containing 3 mg/ml of CYH or 1 mg/ml of G418, respectively) and in non-selective media.

Figure 11:
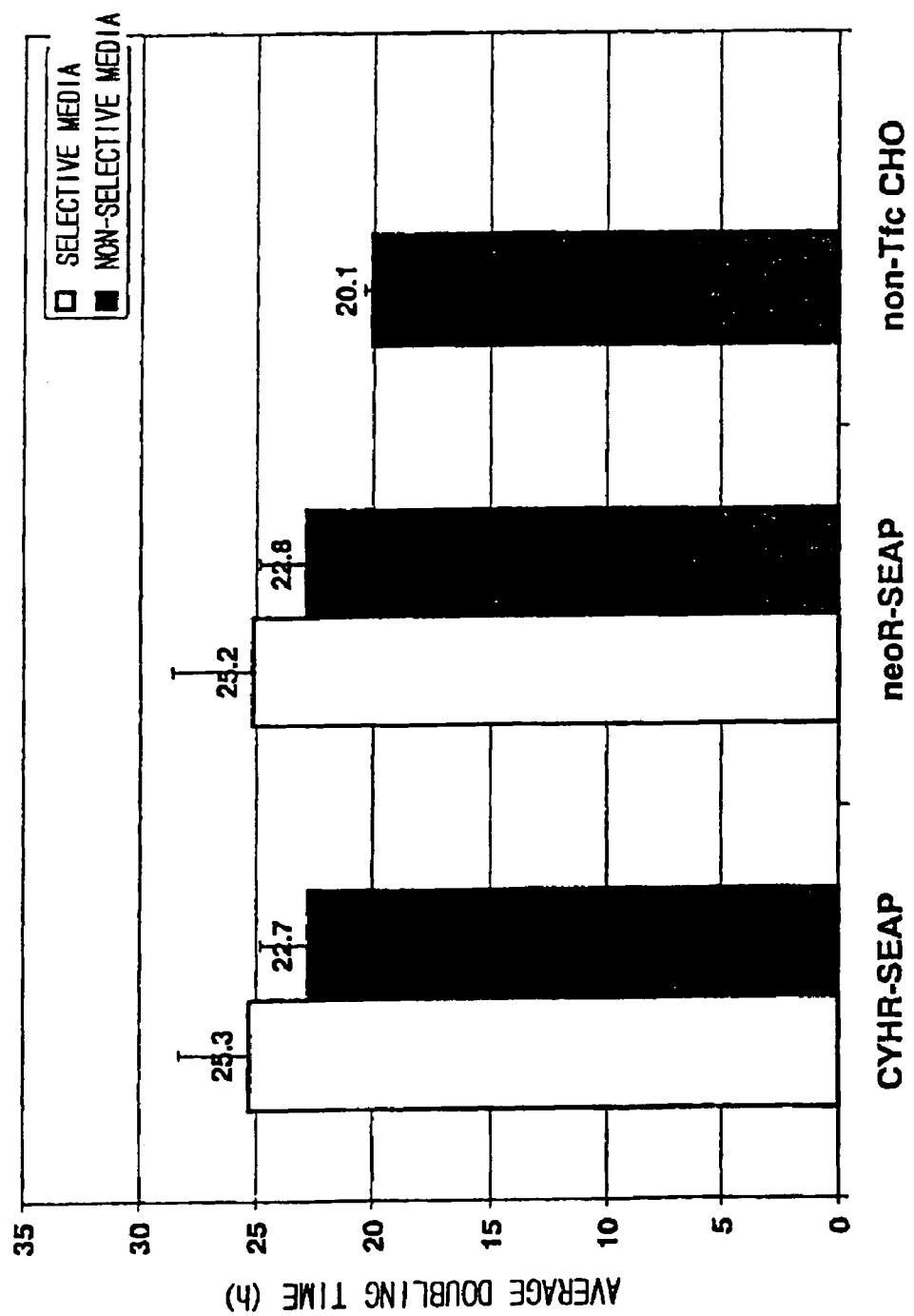

FIG. 11 illustrates the average doubling times of the CYH resistant alkaline phosphatase expressing clones and the G418 resistant alkaline phosphatase expression clones.

15 clones randomly selected from the CYH resistant clones and the G418 resistant clones were subcultured in selective media (containing 3 mg/ml of CYH or 1 mg/ml of G418, respectively) and in non-selective media, respectively, to calculate the average doubling time of each clone in the selective media and the non-selective media. In addition, the average values of the doubling times were also illustrated.

Figure 12:
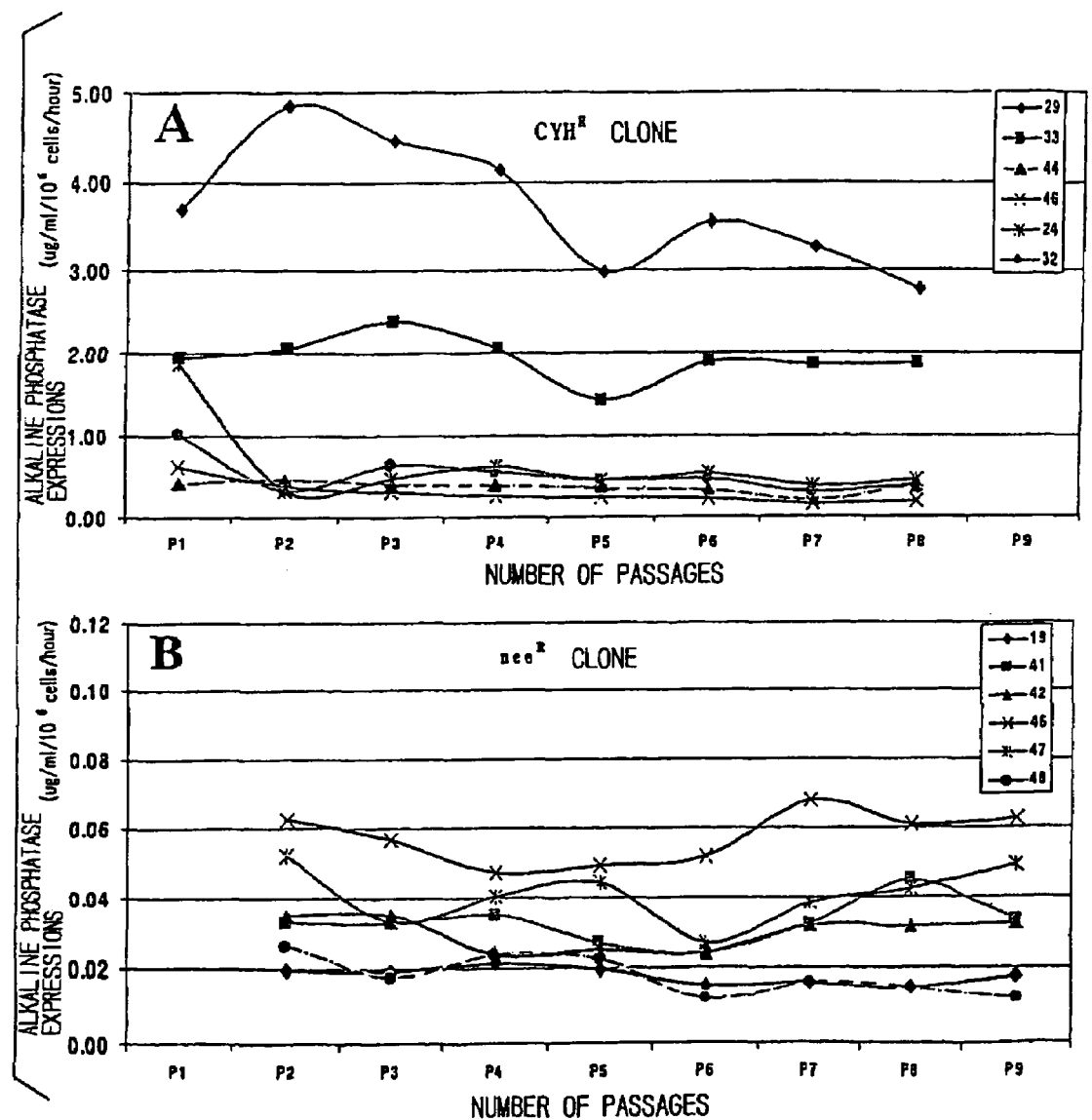

FIG. 12 illustrates the stabilities of the alkaline phosphatase expressions in the CYH resistant clone and the G418 resistant clone.

6 clones selected respectively from the CYH resistant clones and G418 resistant clones were subcultured in selective media (containing 3 mg/ml of CYH or 1 mg/ml of G418, respectively) and in non-selective media, respectively, to measure the SEAP expressions and thus to confirm the stability of the transferred genes.

Figure 13:
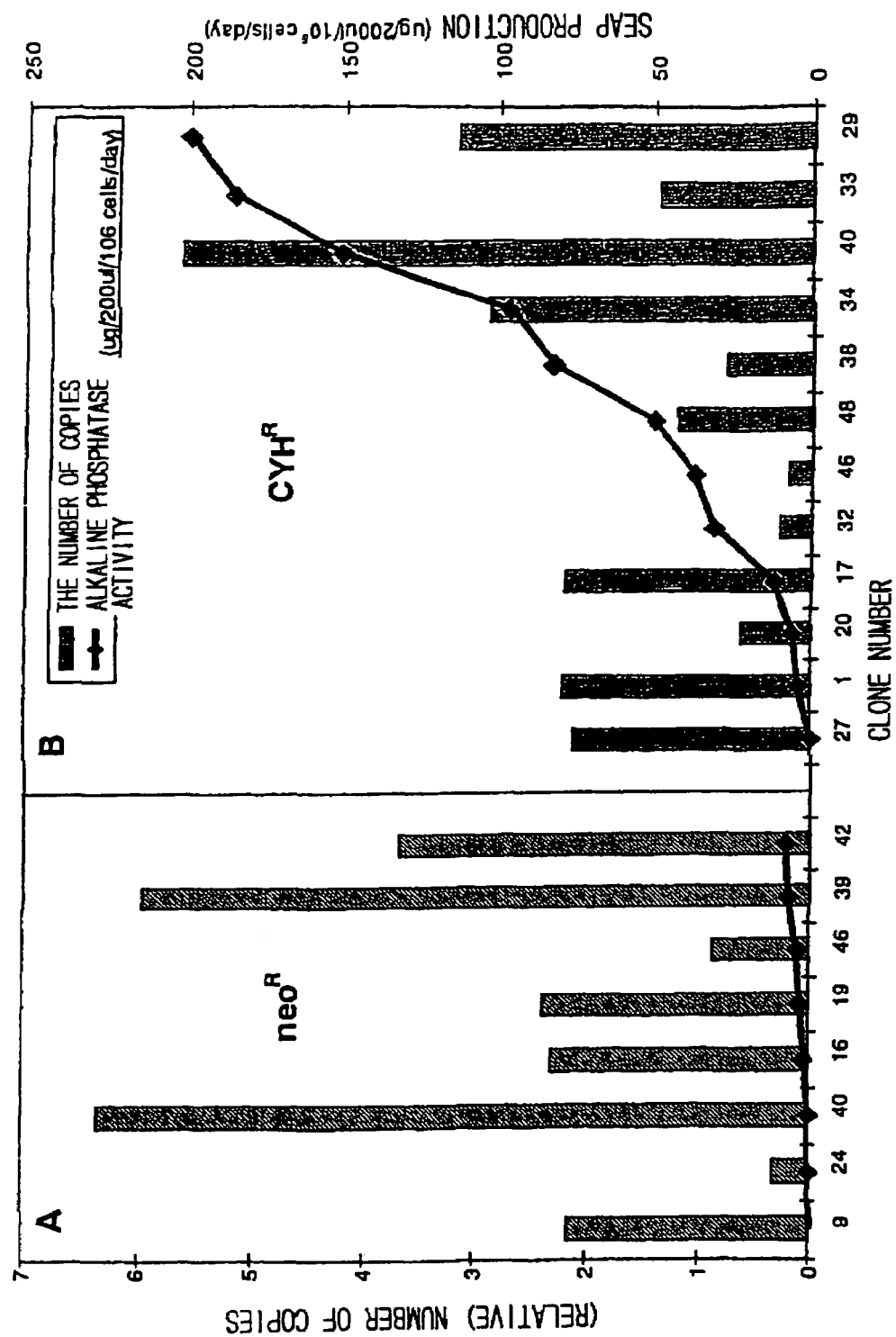

FIG. 13 illustrates the relationship between the alkaline phosphatase expressions and the copy number of the gene in the CYH resistant clone and G418 resistant clone.

Among the SEAP gene transduced clones, 8 clones from the G418 resistant clone and 12 clones from the CYH resistant clone were subjected to the analysis of the number of copies of the SEAP gene by quantitative PCR.

BEST MODE FOR CARRYING OUT THE INVENTION

In the present invention, the protein synthesis inhibitor resistant gene typically includes for example a cycloheximide resistant gene. The present invention is described in detail with reference to the preferred embodiments in the following.

<Cycloheximide Resistant Gene>

Cycloheximide (referred to hereinafter as CYH) is a protein synthesis inhibitor acting on many eucaryotes, and is known to exhibit inhibitory effects by suppressing the extension reaction of a peptide chain through acting on the 60S large subunit of a ribosome in which the mRNA translation reaction is carried out.

As described herein, the phraseology "protein synthesis inhibitor resistant gene" (typically "cycloheximide resistant gene") means a gene which enables imparting the resistance to the protein synthesis inhibitor (typically, CYH) and particularly enables imparting the resistance to the protein synthesis inhibitor (typically, resistance to CYH) to animals or animal cells sensitive to the protein synthesis inhibitor (typically, sensitive to CYH).

The cycloheximide resistant gene as a typical embodiment of the present invention is a gene which can impart the resistance to cycloheximide to cycloheximide sensitive animal cells and has a sequence derived via substitution with a gene encoding a ribosome-constituting protein which is the place of an animal derived protein synthesis. The above described ribosome (particularly 60S large subunit)-constituting protein derived from animals is preferably a protein derived from mammals, more preferably a protein derived from human.

An appropriate specific example of the cycloheximide resistant gene according to the present invention is a gene which encodes the mutant protein L36a in the 60S large subunit of the ribosome in an animal cell or a homologous protein thereof which has become resistant to CYH by the substitution-mutation of a protein L36a or a functionally equivalent homologous protein thereof. Accordingly, the typical embodiment of the gene of the invention is a cycloheximide resistant gene capable of imparting animal cells sensitive to cycloheximide the resistance to cycloheximide and having a sequence mutated via substitution of a gene encoding the animal-derived ribosomal protein L36a (preferably mammal-derived, more preferably human-derived ribosomal protein L36a) or a homologous protein thereof. In this connection, it is preferred that the above described protein encoded by the gene in which mutation via substitution is introduced is a homologous protein of the animal cell protein (protein synthesis inhibitor sensitive, typically CYH sensitive) as a host, or that the animal cell possesses the L36a homologous protein. As described herein, the term homologous protein means the proteins in which two relating proteins have at least 90% of homology between their amino acid sequences.

One of the specific preferred examples of the substitution-mutation according to the present invention is, as will be described in the following examples, the construction of a CYH resistant gene comprising substituting the amino acid proline at the position 54 in the protein encoded by the L36a gene obtained from a human cDNA library by glutamine.

In addition, various proteins derived from the following animals are included in the above described homologous proteins of the present invention, and all of the cycloheximide resistant genes obtained by the substitution-mutation of a gene coding for these homologous proteins are also included in the genes of the present invention.

In human body is present an L44 gene having 99% of a sequence identity with the L36a gene (having 99% of identity in corresponding amino acid sequences), which has a substitution of the amino acid at the position 38 by lysine (cf. arginine in L36a). This gene has functions and sequence substantially equivalent to those of the L36a gene, and is believed that it can function or be used as a CYH resistant gene by substituting the corresponding amino acid proline at position 54 by glutamine. In addition, the mouse or rat L44 genes have totally the same sequence as the human L44 gene, and the porcine L44 gene lacks a residue (at the position 52 in the corresponding amino acid sequence). These genes are believed the same or substantially the same as the human L44 gene in their functions and sequences.

As described above, it is believed that since all of the homologous genes of the mammalian L36a genes of which the DNA sequences have already been confirmed have a high conservation ability of amino acid sequences, any homologous genes of the mammal derived L36a genes (genes encoding the above described homologous proteins), among which an amino acid as the determinant of the sensitivity to CYH, for example proline at the position 54 in the L36a protein and proline at the position 53 in the porcine L44 protein, has been subjected to an appropriate mutation via substitution, for example substitution by glutamine, can be used as the CYH resistant gene. Furthermore, it is predicted that when proteins including the ones derived from animals other than mammals have sufficiently high homologies of the amino acid sequences (90% or more as described above) and an amino acid as the determinant of the sensitivity to CYH, for example at the position 54 in the L36a protein and at the position 53 in the porcine L44 protein, has been subjected to an appropriate mutation via substitution (e.g., by glutamine), proteins derived from the other animals can be used as the CYH resistant marker gene of the present invention to animal cells. This can be confirmed by carrying out a transfection experiment into animal cells according to a process for selecting the cycloheximide resistant animal cell strains of the present invention or a process described herein, that is, a process for selecting cycloheximide resistant animal cell strains comprising transfecting an expression vector containing the cycloheximide resistant gene of the present invention and a foreign protein gene into cycloheximide sensitive animal cells, culturing the cells, and selecting cells with the cycloheximide resistant gene as a selective marker, more particularly a selection process described hereinafter in Example 4.

On the other hand, it remains unclear whether the L41 gene derived from the yeast C. utilis, which has already been described on the applications as the CYH resistant gene, can be complemented functionally due to the low homology of the amino acid sequence to that of the human L36a gene in the level of 7.7%. Moreover, proteins encoded by the L41 gene which has also been confirmed in C. elegans or C. maltosa have a low homology to L36a, and thus these genes are not included in the genes for constructing the cycloheximide resistant gene of the present invention.

A gene of the preferred embodiment in another aspect of the present invention is the cycloheximide resistant gene which can impart the resistance to cycloheximide to animal cells which are sensitive to cycloheximide and codes for amino acid sequences represented by SEQ ID NO: 1 or 2 or amino acid sequences in which one or several amino acids have been substituted, deleted, inserted or added. In this connection, SEQ ID NO: 1 is the sequence of the human derived ribosomal protein L36a (SEQ ID NO:11) in which proline at the position 54 has been mutated via substitution by glutamine, and SEQ ID NO: 2 is the sequence of the human derived ribosomal protein L44 (SEQ ID NO:12) in which proline at the position 54 has been mutated via substitution by glutamine. This embodiment includes all of the cycloheximide resistant genes capable of imparting the resistance to cycloheximide to animal cells sensitive to cycloheximide and having a sequence mutated via substitution on the gene coding for the above described homologous proteins.

<Construction of Cycloheximide Resistant Gene>

Typical embodiment of the present invention has been intended to provide a CYH resistant gene as a novel marker gene for transduction on the basis of the animal cells being sensitive to CYH. That is to say, there have been examined whether a CYH resistant gene can be constructed by cloning and modifying a gene of a ribosomal protein derived from, an animal and the a foreign protein production system can be developed with an expression vector constructed with the marker gene. The following description illustrates the L36a protein as a protein constituting a ribosome derived from an animal. In order to constitute the present invention, a gene of the human L36a protein is first isolated and cloned as a homologous gene to the yeast L41 protein. Specifically, the gene may be cloned from the human cDNA library by using an oligonucleotide synthesized from the well-known DNA sequence as a probe. While the cDNA of the L36a gene has been cloned with Gene Trapper cDNA Positive Selection System (Gibco BRL, Cat. No. 10356-020) in Examples of the present invention, it is also possible to conduct cloning by the other methods, for example, by hybridization with a labeled probe from a phage library or a plasmid library. These methods may be carried out according to the description by J. Sambrook, E. F. Frisch, T. Maniatis; Molecular Cloning 2nd edition, Cold Spring Harbor Laboratory, 1989.

In order to construct a CYH resistant gene from the cloned L36a gene, the CYH resistant gene (marker gene) which confers the resistance to CYH was constructed by three steps of PCR with a primer which has been designed in the examples of the present invention to ensure that the corresponding amino acid at the position 54 of the L36a gene should become glutamine and with the L36a gene as a template (see base sequence of SEQ ID NO: 1 in Sequence Listing). The gene of the present invention thus amplified by PCR can be cloned with commercially available vectors such as TA Cloning Kit (Invitrogen) and pBluescriptII (Stratagene). Any appropriate methods may be employed for altering the amino acid sequence to the resistant type, and for example site-directed mutagenesis with a mismatch primer can be employed. This method has been described in detail in the above described literature Molecular Cloning, 2nd edition. Furthermore, the gene of the present invention can also be prepared by the chemical synthesis of a nucleic acid according to the ordinary methods such as the phosphite triester method (Hunkapiller, M. et al., Nature, 310, 105, 1984) on the basis of the polynucleotide sequence informations represented by SEQ ID NO: 1 or 2. In addition, it is possible to construct the CYH resistant gene by introducing an amino acid mutation into the L36a gene available from public DNA databases, using the PCR, site-directed mutagenesis, chemical synthesis method and the like, on the basis of the sequence informations of functionally homologous known genes so that the amino acid corresponding to the amino acid at the position 54 of the L36a gene should be glutamine. The base sequence of the DNA thus obtained can be confirmed by analysis according to for example the Maxam-Gilbert method (Maxam, A. M. and Gilbert, W., Proc. Natl. Acad. Sci., U.S.A., 74, 560, 1977), and the Sanger method (e.g., Sanger, F. & A. R. Coulson, J. Mol. Biol., 94, 441, 1975; Sanger, F. & Nicklen and A. R. Coulson., Proc. Natl. Acad. Sci. USA, 74, 5463, 1977).

<Construction of a Vector Containing a Selective Marker Gene>

The present invention also relates to a recombinant vector containing the above described protein synthesis inhibitor resistant gene (typically, CYH resistant gene), and an expression vector containing the protein synthesis inhibitor resistant gene and a foreign protein gene.

With respect to expression of the protein synthesis inhibitor resistant gene in host cells according to the present invention, the gene of the present invention can be expressed in a host cells by using a vector in which the gene operably coupling with a regulatory sequence such as a promoter sequence and a terminator sequence is inserted. As described herein, the phraseology operably coupling means that in a host into which the gene according to the present invention, the regulatory sequence is coupled with the gene according to the present invention to ensure that the gene is expressed under the control of the regulatory sequence. It is generally possible to couple the promoter in the 5'-upstream of the gene and the terminator in the 3'-downstream of the gene.

The promoter used is not specifically limited and may be the one exhibiting promoter activities in host cells to be transformed. The promoter region on a chromosome in which the L36a gene is originally expressed may be used for the expression, and in the present invention in which the host for transformation is the animal cells, the other promoters including an early or late promoter of adenovirus (Ad), an early or late promoter of simian virus 40 (SV40), a thymidine kinase (tk) gene promoter of herpes simplex virus (HSV), promoters obtained from viral genomes of *Rous sarcoma* virus, cytomegalovirus, *mouse papilloma* virus, *bovine papilloma* virus, *avian sarcoma* virus, retrovirus, hepatitis B virus and the like, promoters derived from mammals such as an actin promoter or an immunoglobulin promoter, and heat shock protein promoter, may be employed.

The recombinant DNA vector according to the present invention is not specifically limited and may be the one in which the CYH resistant gene has been transduced in a form to be expressed in host cells. For instance, such vector as pCI-neo (Promega) may be constructed by linking the CYH resistant gene in a form operable to a vector (typically a plasmid) in which promoter and terminator sequences functioning in animal cells have preliminarily contained. It is also possible to construct the recombinant vector of the present invention by linking the CYH resistant gene which has become operable, for example, with a CMV early gene promoter and a SV40 late gene terminator and a plasmid vector pUC18 (Takara Shuzo Co., Ltd.) containing an ampicillin resistant gene and *Escherichia coli* replication origin (ColE1 ori), or a plasmid such as pBluescriptII (Stratagene) and pBR322. In addition, if necessary, the recombinant vector according to the present invention may be used in combination with the other selective marker genes such as the G418 resistant gene or with a gene which enables gene amplification such as a dhfr gene. It will be possible to efficiently amplify the gene of a plasmid containing a foreign protein gene (expression vector) and the dhfr gene with methotrexate after transferring the selective marker gene and the plasmid into a host cell by using dihydrofolate reductase defective CHO cells as the host animal cells for transformation. That is to say, it has been shown that the foreign gene sequence linked physically to the dhfr gene sequence is also amplified (Kaufman R J, Sharp P A, J. Mol. Biol., 25:601, 1982, Christman J K, et al., Proc. Natl. Acad. Sci. USA., 79:1815, 1982). Furthermore, the expression vectors can be linked to a signal sequence, if desired, to harvest the expression product of the target foreign gene with ease.

In addition, it is also possible to transduce a reporter gene with which the activity can be easily measured to the recombinant vector of the present invention for ensuring that a clone in which the foreign gene is highly expressed can be easily selected. As the reporter gene, there may be used for example a GFP gene encoding a green fluorescent protein. A clone expressing highly the GFP gene can be conveniently concentrated for example by flow cytometry as described in Example 5.

As for the general methods for constructing the recombinant vector and the expression vectors, it is possible to refer to literatures such as Molecular Cloning 2nd edition, which will be incorporated in Examples below.

<Foreign Gene Which may be Transduced by the Selective Marker Gene>

It is possible to express a foreign gene, at a high level, encoding the desired polypeptide in host cells with the expression vector according to the present invention. Such polypeptides include the followings.

Typical polypeptides include various monoclonal antibodies, cytokines (for example, interferon (IFN) α, β, γ, tumor necrosis factor (TNF), lymphotoxin (LT), interleukin (IL) 1-13, granulocyte colony-stimulating factor (G-CSF), granulocyte-macrophage colony-stimulating factor (GM-CSF), stem cell factor (SCF), leukemia inhibiting factor (LIF), erythropoietin (EPO), nerve growth factor (NGF), epidermal growth factor (EGF), fibroblast growth factor (FGF), hepatocyte growth factor (HGF), platelet-derived growth factor (PDGF), vascular endothelial growth factor (VEGF), growth hormone (GH), insulin-like growth factor (IGF), transforming growth factors such as TGFα and TGFβ, and the like), virus antigen proteins (for example, antigen proteins of human immunodeficiency virus (HIV), human hepatitis B virus (HBV), human hepatitis C virus (HCV), herpes simplex virus (HSV), cytomegalovirus (CMV), adult T cell leukemia virus (ATLV), influenza virus, Japanese encephalitis virus, rubella virus, measles virus, and the like), various receptors (for example, G protein-coupled receptor (GPCR), cytokine receptor, nuclear receptor, and the like), various gene expression regulatory proteins, superoxide dismutase, α-1-antitrypsin, insulin, proinsulin, vesicle stimulating hormone, calcitonin, luteinizing hormone, glucagon, blood coagulation factors such as factor VIIIC, factor IX, factor Xa, tissue factor, and willebrand factor, anticoagulant factors such as protein C, atrial natriuretic factor, pulmonary surfactant, plasminogen activators such as urokinase and human urinary or tissue plasminogen activators (t-PA), bombesin, thrombin, enkephalinase, human macrophage inflammatory protein (MIP-1-α), serum albumins such as human serum albumin, mouse gonadotropin relating peptides, inhibin, activin, and the like.

In the present invention, the expression vectors, which comprise the CYH resistant gene and the foreign protein gene in the form to be expressed, are not specifically limited.

<Host Cells Which may be Transformed with the Selective Marker Gene of the Present Invention>

Host cells in which transduction may be carried out with the selective marker gene, that is the protein synthesis inhibitor resistant gene of the present invention (typically cycloheximide resistant gene) are protein synthesis inhibitor sensitive cells (typically cycloheximide sensitive cells) derived from any animals, particularly mammals. For instance, examples of useful mammalian host cells include simian kidney derived lines transformed with SV40 (COS7 cells), human embryonic renal lines (293 cells), baby hamster kidney cells (BHK cells), Chinese hamster ovary cells (CHO cells, particularly CHO (DHFR$^-$) cells (ATCC, CRL-9096)), mouse Sertoli cells (TM4 cells), simian renal cells (CV1 cells), african green monkey renal cells (VERO cells), human uterocervical carcinoma cells (HeLa cells), canine renal cells (MDCK cells), buffalo rat liver cells (BRL3A cells), human pulmonary cells (W138 cells), human liver cells (HepG2 cells), TRI cells, MRC5 cells, FS4 cells, and the like. Furthermore, it is also possible to use myeloma cells used as cells for cell fusion, hybridoma cells obtained by fusing these cells with a variety of lymphocytes or spleen cells.

In addition, the useful host cells for practice of the present invention include multipotential embryonic stem cells (ES cells). The ES cells can be obtained from pre-implantation embryo cultured in vitro. These cells can be cultured, and also differentiated in vitro (Evans, N. J. et al., Nature, 292, 154–156, 1981). Such ES cells can be derived from any one of various species including Primates such as human, useful cattle such as cows, pigs, sheep and goat, rats, rabbits, mice, and the like. Among those, the ES cells derived from cattle such as cows, pigs, sheep and goat, which can be used as a host for producing a foreign protein and derived from experimental animals such as rats and mice are appropriate hosts. Transformed ES cells selected with the marker gene have high possibilities that the desired protein is highly expressed, and thus the desired protein can be expected to be expressed in a high level in an animal obtained with the transformed ES cells.

Among these animal cells, the CHO cells derived from Chinese hamster ovary are preferred, and the dihydrofolate reductase defective CHO cells (DHFR$^-$ cells) are more preferred.

Furthermore, the animal cells are generally sensitive to protein synthesis inhibitors, and this can be easily confirmed by culturing the cells in a medium containing the inhibitor.

The above described various animal cells can be easily available from American Type Culture Collection (ATCC) and the other preservation organizations, and are also commercially available from The Institute of Physical and Chemical Research, Plant Cell Bank, and the like.

<Transformation of Animal Cells and Selection of the CYH Resistant Clones>

The present invention also relates to the transformed animal cells containing the above described expression vectors of the present invention, and a process for selecting a protein synthesis inhibitor resistant animal cell strain comprising culturing the transformed animal cells, and selecting a cell strain with a protein synthesis inhibitor resistant gene (typically, cycloheximide resistant gene) as a selective marker.

As the methods for transfecting the expression vectors of the present invention, in a typical embodiment, containing the CYH resistant gene into animal cells, there may be used the calcium phosphate precipitation method (Graham, van der Eb, Virology, 52:456, 1973) as well as the other well-known methods such as the microinjection method (Capecchi, M R, Cell, 22:479, 1980), the electroporation method (Zimmermann, U., Biochim. Biophys. Acta, 694:227, 1982), the liposome method (Mannino, R. J., Gould-Fogerite, S., BioTechniques, 6:682, 1988), and the like. In any case of the transfection experiments, transfected cells may be cloned by changing the medium into the one containing CYH generally 1–3 days after the plasmid DNA has been transfected into animal cells. By way of example, when transfection is carried out by the liposome method with the CHO cells as host cells, the procedure is generally conducted as follows. First, 1 µg of a plasmid and 6 µl of Lipofectamine reagent (Gibco BRL, 18324-012) are mixed and left standing at room temperature for 30 minutes and then added to $5\times10^5$ CHO cells. The medium is changed after 16 hours for culturing the mixture for further 24 hours, and then cells are collected. The collected cells are diluted, seeded again on a dish having a diameter of 10 cm, and cultured for 24 hours, after which the medium is changed into the one containing CYH in a concentration of 3 µg/ml–10 µg/ml in order to culture the mixture for further 2–3 weeks, and thus a CYH resistant transduced clones can be selected.

The following method can be used in order to separate rapidly the CYH resistant clones from non-transformed cells. That is to say, the cells collected after transfection are diluted, and seeded on, for example, a 24-well plate for culturing. After the cells have been cultured in a medium having CYH added thereto for about 1 week, the cells are once recovered by trypsin treatment and seeded again on, for example, a 24-well plate for culturing for further 1 week. It will be possible to remove the non-transformed cells attached on the surface of the plate and to recover only the transformed cells by this additional recovering and reseeding step, and thus it can shorten the isolation time of the stable gene expressing cell.

The present invention also relates to a process for producing a protein comprising culturing the above described transformed cells of the present invention, collecting an expressed foreign protein from the culture.

Transformed animal cells can be cultured by well-known methods, and thus Molecular Cloning, Current Protocols and the like described hereinafter in Examples can be referred. As the medium, there may be used, for example, MEM, DMEM and RPMI1640 media containing ca. 5–20% of fetal bovine serum. The pH value is preferably in the range of ca. 6–8. Culturing can be carried out generally at ca. 30–40° C. in the presence of 5% $CO_2$ for about 15–60 hours, and continued with changing the medium every several days. When the cells have been grown to a confluent level, the cells are dispersed into individual ones generally with an about 0.25% trypsin PBS solution, diluted to several times, and seeded in a new culture vessel for further culturing. When the cells have been grown to the aimed amount, these cells are harvested. Subculture can be thus conducted to expand a culturing scale to an optional one.

Expression of the transferred gene can be checked by the methods such as for example the northern blotting assay or RT-PCR with RNA recovered from cells, the ELISA assay or western blotting assay with an antibody of the expressed protein, or the detection of enzyme activity in the culture medium or cells in case of the protein being an enzyme. When the foreign gene to be expressed is GFP, the expression level can be measured by analyzing the recovered cells by flow cytometry. Since a very high correlation is observed between the expression amount of GFP and the intensity of fluorescence obtained by FACS analysis, it can be thought the intensity of fluorescence as the GFP expression. When the foreign gene to be expressed is an alkaline phosphatase gene and a β-galactosidase gene, it is possible to examine the amount of expression by measuring the respective enzyme activities.

While the desired foreign protein is recovered from a culture (containing a medium and cells), preferably from the medium as a secretory polypeptide, it can be also recovered from a host cell lysate when it has been directly expressed without any secretory signal sequence. When the desired protein has been expressed in recombinant cells derived from non-human, the target product contains no other proteins or polypeptides derived from human. However, it is preferable to purify the target product from the other protein or polypeptide derived from the recombinant cells and thus to obtain a substantially uniform product in relation to the target expression product. As the first stage therefor, an ordinary medium (containing cells) or a cell lysate is centrifuged to remove cells or cell debris. Next, the target product is purified by the means for isolating and purifying a protein from the other proteins and polypeptides contaminated, for example, fractionation with immunoaffinity or ion exchange columns; ethanol precipitation; reverse phase HPLC; chromatography with cation exchange resins such as silica or DEAE, e.g. gel electrophoresis with Sephadex G-75; or chromatography with a plasminogen column to which the target product is linked in order to remove contaminates such as IgG and the like, and with a protein A Sepharose column. These methods can be referred to, for example, Guide to Protein Purification Methods in Enzymology, vol. 182, edited by Deutscher, Academic Press, and the other.

It is possible, according to the present invention, to select efficiently a cycloheximide resistant cell clone and to obtain the expression product of the desired foreign gene highly expressed as a purified product.

EXAMPLES

The present invention will be further illustrated with reference to the following Examples, but the scope of the present invention is not limited thereto.

A variety of experimental techniques relating to recombination of genes such as cloning described hereinafter have been carried out according to the methods of genetic engineering described in the literatures by J. Sambrook, E. F. Frisch, T. Maniatis; Molecular Cloning 2nd edition, Cold Spring Harbor Laboratory, 1989, and Frederick M. Ausubel et al., Ed., Current Protocols, Current Protocols in Molecular Biology.

Example 1

Cloning of Human L36a Gene

It has been confirmed by searching public DNA databases that a human gene homologous to the yeast L41 gene is the L36a gene (GI 4506651). The homology of the amino acid sequences of Candida utilis L41 and L36a is illustrated in FIG. 1. An oligonucleotide HL36G1 (5'-AGA AGT GTG GCA AGC ATC AG-3', SEQ ID NO: 3) was chemically synthesized and used as a probe. The cDNA of the L36a gene was cloned from the cDNA library (Superscript Human Fetal Brain cDNA Library, Life Technologies, Cat. No. 10662-013) derived from human embryonic brain with Gene Trapper cDNA Positive Selection System (Gibco BRL, Cat. No. 10356-020). Cloning was performed according to the attached manual. Specifically, the double-stranded DNA library in which cDNA has been inserted into the NotI-SalI site of a vector pCMV•SPORT for the expression of animal cells was denatured to be the single-stranded structure, and a hybrid was formed with HL36G1 having a biotin label. The hybrid thus formed was adsorbed in magnetic beads coated with streptavidin to concentrate the L36a cDNA clone. After concentration, the DNA was converted again into the double-stranded DNA with a non-labelled HL36G1 as a primer in order to transform Escherichia coli Ultramax attached to a kit. Among the transformants thus obtained, plasmid DNAs were extracted from 40 clones by the ordinary method to select clones in which L36a is contained. The selection was conducted by PCR. PCR was carried out with Ex Taq polymerase (Takara Shuzo Co., Ltd.) under the condition of PCR ((30 seconds at 94° C., 1 minute at 55° C., 2 minutes at 72° C.)×25 cycles). The primers used were HL36G1 as a forward primer, and 5'-CTC CTC CCA GTT CAA AAT GC-3' (HL36RT1, SEQ ID NO: 4) as a reverse primer. As a result, it has been confirmed that the L36a gene is contained in 14 clones among 40 clones. A cDNA fragment was excised from these plasmids with restriction enzymes NotI and SalI, and the length of the fragments was checked by agarose gel electrophoresis. Furthermore, 6 clones having a long insert DNA fragment among these clones were checked on their sequences, and it has been clarified that every clone contains the full length of the ORF comprising 318 bases of the L36a gene.

Example 2

Construction of Cycloheximide Resistant Gene and Confirmation of its Function

In order to confer the resistance to CYH on the human L36a gene, mutation in which the amino acid proline at the position 54 is substituted by glutamine was introduced. Specifically, in order to convert the base C at the position 167 of ORF into A, 3 steps of PCR was performed with four chemically synthesized primers as illustrated in FIG. 2. Specifically, PCR was first performed with a combination of the forward primer 1 (5'-GGG TCT AGA ATG GTC AAC GTA CCT AAA AC-3', SEQ ID NO: 5) and reverse primer 3 (5'-CCG GAA AAT TTG CTT TGT CTG CCC A-3', SEQ ID NO: 6) and a combination of the forward primer 4 (5'-GGG CAG ACA AAG CAA ATT TTC CGG-3', SEQ ID NO: 7) and the reverse primer 2 (5'-GGG TCT AGA TTA GAA CTG GAT CAC TTG GC-3', SEQ ID NO: 8) in the presence of the L36a gene as a template. PCR was carried out with Ex Taq polymerase (Takara Shuzo Co., Ltd.) under the condition of PCR ((30 seconds at 94° C., 1 minute at 55° C., 2 minutes at 72° C.)×25 cycles). After the two PCR products thus obtained were purified with High Pure PCR Product Purification Kit (Roche, 1-732-668), PCR ((30 seconds at 94° C., 1 minute at 55° C., 2 minutes at 72° C.)×25 cycles) was performed with the forward primer 1 and the reverse primer 2 in the presence of the mixture as a template to give the CYH resistant L36a gene (L36a-CYH$^R$) to which the recognition sites of the restriction enzyme XbaI have been added at both termini (SEQ ID NO: 1 and 3). The ca. 0.3 kb DNA fragment thus amplified was digested with XbaI, and then cloned into the XbaI site of pUC18. Dye Terminator Cycles Sequence Kit (Perkin-Elmer) was used for determining the nucleotide sequence of the amplified DNA fragment, and after confirming the nucleotide sequence of the gene obtained, the XbaI fragment containing the L36a-CYH$^R$ fragment was inserted into the XbaI site at the downstream of the CMV early gene promoter region of the animal cell expressing vector pCI-neo (Promega, Cat. No. E1841) to give a plasmid pCI-neo-L36.

In order to check whether the constructed L36a-CYH$^R$ gene confers the resistance to cycloheximide on animal cells, transfection experiment into Chinese hamster derived CHO (DHFR) cells (ATCC, CRL-9096, referred to hereinafter as "CHO cells") was performed. Specifically, 1 μg of the plasmid pCI-neo-L36 or pCI-neo was co-transfected together with 0.1 μg of plasmid pSEAP2-control (Clontech, 6052-1) containing secretory alkaline phosphatase SEAP into the CHO cells. Transfection experiment was performed according to the method described in Example 4, and the plasmids were transfected into $1\times10^5$ of the CHO cells cultured on a 24-well plate overnight. After culturing for 24 hours, the cells were washed twice with the medium, and the medium was changed into the ones containing CYH in the concentration of 0 and 10 mg/ml, respectively. After 4 and 8 hours, a portion of the supernatant was recovered, and the SEAP activity was measured. The activity after 8 hours based on the activity after 4 hours as 1 was 2.17 (CYH, 0 mg/ml), 1.44 (CYH, 10 mg/ml) in pCI-neo-L36, and 2.15 (CYH, 0 mg/ml), 1.09 (CYH, 10 mg/ml) )in pCI-neo (FIG. 4). It has been confirmed from the result that pCI-neo-L36 confers the resistance to CYH on the CHO cells, the cells into which the plasmid has been transferred live even in the presence of CYH, and the reporter gene on the co-transfected plasmids is expressed.

Example 3

Construction of Expression Plasmid

Three reporter genes were respectively transferred into the BamHI site of pCI-neo-L36 in an opposite direction to the neo gene to construct the expression vectors containing L36a-CYH$^R$. As the reporter gene, a green fluorescent protein having short half life d2EGFP (pd2EGFP-N1 derived, Clontech, 6009-1) and a β-galactosidase (b-galactosidase; lacZ) gene (pCH110 derived, Pharmacia, 27-4508-01), both of which are the reporters accumulated intracellularly and an alkaline phosphatase secreted extracellularly SEAP (pSEAP2-control derived, Clontech, 6052-1) were used.

The structures of the expression vectors in which each of the three reporter genes has been transferred are illustrated in FIG. 5, and referred to as pL36a-neo-GFP, pL36a-neo-lacZ, pL36a-neo-SEAP, respectively. The vectors pNeo-SEAP and pNeo-lacZ having the same structure as pL36a-neo-lacZ and pL36a-neo-SEAP, respectively, except that L36a-CYH$^R$ is not contained were also constructed for control experiments.

These plasmids were constructed as follows. The plasmid pd2EGFP-N1 was digested with BglII and BamHI prior to self-ligation to remove the multi-cloning site between the promoter and the d2EGFP gene. Subsequently, the plasmid was digested with PshBI and AflII to excise the 1.7 kb DNA fragment containing CMV early gene promoter+d2EGFP gene+SV40 derived poly A signal. The fragment DNA termini were blunted with Klenow fragment, to which end the BamHI linker (5'-CCCGGATCCGGG-3' (SEQ ID NO:15), Takara Shuzo Co., Ltd., 4810P) was ligated before further digestion with BamHI, and was inserted into the BamHI site of pCI-neo-L36 to construct pL36a-neo-GFP. The plasmid pCH110 was digested with NcoI and blunted with Klenow fragment prior to the addition of the BamHI linker. A 3.9 kb DNA fragment containing SV40 early gene promoter+lacZ gene+SV40 derived poly A signal was excised by further digestion with BamHI, and inserted into the BamHI site of pCI-neo-L36 or into the BamHI site of pCI-neo to construct pL36a-neo-lacZ and pNeo-lacZ, respectively. The plasmid pSEAP2-control was digested with SalI and blunted with Klenow fragment, and then the BglII linker (5'-CAGATCTG-3', Takara Shuzo Co., Ltd., 4621P) was ligated. A 2.3 kb DNA fragment containing SV40 early gene promoter+SEAP gene+SV40 derived poly A signal+SV40 derived enhancer sequence was excised by further digestion with BglII and BamHI, and inserted into the BamHI site of pCI-neo-L36 or into the BamHI site of pCI-neo to construct pL36a-neo-SEAP and pNeo-SEAP, respectively.

Example 4

Cell Culture and Transfection Experiment

In order to culture the CHO cells, fetal calf serum (FCS; Gibco BRL, 26140-087) in the final concentration of 10% was added to □-MEM (Gibco BRL, 12571-063) to which antibiotics (Penicillin-Streptomycin, Gibco BRL, 15070-089) have been added, and the medium was used as a medium for subculture. The CHO cells used in the transfection experiment were seeded at a density of $5\times10^5$ on a dish having a diameter of 10 cm for culturing attached cells, and recovered after three days. The cells recovered were seeded on a dish having a diameter of 6 cm at a density of $5\times10^5$, and transfection was performed by the lipofection method after 24 hours. Specifically, 1 μg of the plasmid and 6 μl of Lipofectamine reagent (Gibco BRL, 18324-012) were mixed, left standing at room temperature for 30 minutes, and the mixture was added dropwise to the cells which have been moved in a medium without antibiotics and serum. After 16 hours, the medium was changed into the one for sub-culture, the cells were further cultured for 24 hours and recovered, and the transfected cells were selected so that the cells are appropriate to the CYH resistant marker and the control neo marker, respectively.

When the transfected clones are selected on the basis of the resistance to CYH, the recovered cells were diluted four times with a medium to which CYH has not been added, and seeded again on a dish having a diameter of 10 cm. After 24 hours, the medium was changed into the one containing CYH (3 mg/ml) and the culture was continued for further 2–3 weeks. The resulting CYH resistant colonies were isolated with a cloning ring, seeded again on a 24-well plate, and then cultured in the medium to which CYH has not been added. Also, the clones, into which the CYH resistance has been transduced, could be isolated by diluting the cells and culturing the cells on a 24-well plate after the transduction experiment. That is to say, the recovered cells were seeded on about 10 of 24-well plates and cultured in the presence of CYH. After culturing for 1 week, the cells were recovered in order to remove the CYH sensitive cells. The recovered cells were cultured again on 24-well plates for further culturing for 1 week, and thus the CYH resistant stain could be rapidly isolated.

When the transformed clones are selected on the basis of the resistance to G418, the cells recovered after transfection were diluted to 50 times with a medium containing G418 (1 mg/ml, Gibco BRL, 11811-049), and seeded again in a dish having a diameter of 10 cm. Culturing was carried out for 1–2 weeks until the colonies have been formed. Single colony was isolated with a cloning ring as described above, and seeded again in 24-well plates for culturing in a medium containing G418. Furthermore, it was possible to isolate the resistant clones by the dilution method in the similar manner to the CYH resistant stain. In G418 resistance, cells were seeded in 96-well plates, and cultured in a medium containing G418 for 1–2 weeks for isolating the G418 resistant clones.

Example 5

Comparison of GFP Gene Expressions

Transfected clones were isolated with cloning ring. In the case of CYH selection, the transfected cells were seeded again in 24-well plates and cultured in the absence of CYH for 24 hours, and then the medium was changed into the one to which CYH has been added for culturing for 1 week and trypsin treatment for recovering the cells. In the case of G418 selection, cells were seeded again in 24-well plates, cultured in a medium containing G418 for 1 week, and then recovered. The recovered cells were prepared into cell suspensions of $10^5$–$10^7$ cells/ml with PBS having 0.5% FCS and Propidium iodide (PI; Pharmingen, 66211E) added thereto, and the cell count and the GFP expressions were analyzed by flow cytometry (FACS; FACScan, Beckton Dickinson). Since a very high correlation is observed between the expression amount of GFP and the intensity of fluorescence obtained by FACS analysis, it can be contemplated the intensity of fluorescence as the GFP expression (Meng, Y. G., 2000, Subramanian & Srienc, 1996). Specifically, $5\times10^4$ of cells were measured, and histograms in relation to the number of cells and the intensity of fluorescence derived from GFP are made as illustrated in FIG. 6. The fluorescence intensities were classified into four regions in the increasing order of M1–M4, and the cells included in the region M1 were regarded as the group of cells in which GFP is not expressed, while the cells included in the regions M3 and M4 were regarded as the group of cells in which the expression of GFP is positive. If the fluorescence strength is too high, it exceeds the measuring range, and thus the number of cells of a high expression strain is calculated exceedingly low. In order to avoid such trouble, the amount of expression of GFP was represented by the ratio of the number of cells calculated with equation I:

Ratio of GFP positive cells=(number of cells contained in range $M3$–$M4$)/(number of cells contained in range $M1$–$M4$)     (Equation I):

As a result of analysis of 44 CYH resistant clones and 46 G418 resistant clones, which was obtained as a control by transferring pd2EGFP-N1, 43% of the CYH resistant stain selected randomly showed higher expression than all of the G418 resistant clones, as illustrated in FIG. 7. It has been thus confirmed that the CYH resistance selection produces the clones in which the GFP gene is highly expressed more efficiently than the G418 resistance selection.

In the case of the selective culture of the CHO cells having pL36-neo-GFP transfected therein in a medium having G418 added thereto, the same result as that obtained by transfecting pd2EGFP-N1 was obtained, and thus it is believed that the efficient acquisition of the clones in which the GFP gene is highly expressed is an effect specifically obtained in the selective culture with the L36a-CYH$^R$ gene and CYH (no data is shown).

Example 6

Comparison of the Expression of Alkaline Phosphatase Gene

The transfected cells were isolated by the dilution method. Each of 50 CYH resistant and G418 resistant clones were isolated by transfecting pL36a-neo-SEAP and pNeo-SEAP into cells, respectively, and each clone was cultured in the selective medium in 24-well plates to a 90% confluent level for analyzing SEAP expressions.

SEAP expressions were measured in triplicate continuously as shown in the following.

Each clone was cultured, and $2.5\times10^4$ of the cells were seeded in a 96-well plate and cultured in 200 µl of the selective medium having the drug added thereto for 48 hours. After each clone was washed with PBS(−), the cell concentration of the cell suspension was counted with WST-1 cell proliferation reagent (Boehringer Mannheim, 1-644-807). The supernatant after culturing was stored at −80° C. for measurement in future. The enzyme activity of SEAP was measured with The Great Escape SEAP Chemiluminescence Detection Kit (Clontech, K2041-1). Chemiluminescence was measured with a CT-9000D plate luminometer manufactured by Dia-iatron. The amount of SEAP was quantitatively measured with a calibration curve made by using the standard SEAP attached to the kit. The expression amount of SEAP of each clone was calculated with the following equation 2 with $N_0$ as the number of cells at seeding, N as the number of cells at the end of culturing.

Expression amount of SEAP (µg/$10^6$ cells/day)= {amount of SEAP in medium (µg)}×$10^6$×(ln$N$−ln$N_0$)/($N$−$N_0$)×2(days)     (Equation 2):

It has been found in the analysis of the expression amount of each clone that while 54% of the total CYH resistant clones exhibited expression amounts of 5 mg/$10^6$ cells/day or more, only 8% of the total G418 resistant clones exhibited the equivalent amounts. Furthermore, it has been also found that 20% of the CYH resistant clones exhibited the expression amounts of 30 mg/$10^6$ cells/day or more and 6% exhibited the expression amounts of 100 mg/$10^6$ cells/day or more (FIG. 8). It has been confirmed from these results that the high expression clones can be also acquired efficiently in the SEAP gene stably transfected cell lines in the case of selection based on the resistance to CYH.

Example 7

Comparison of β-Galactosidase Gene Expression

The transfected cells were isolated by the dilution method. 50 CYH resistant clones and 53 G418 resistant clones were isolated by transfecting pL36a-neo-lacZ and pNeo-lacZ, respectively, into the CHO cells.

The activity of β-galactosidase was measured with the Luminescent β-gal detection kit II (Clontech, K2048-1). Specifically, the cells of each clone cultured were seeded at a density of $5\times10^5$ in a dish having a diameter of 6 cm and cultured in a selective medium having a drug added thereto for 2 days. The cells were recovered, lysed with a lysis solution attached to the kit for preparing a cell lysate for assay.

It has been found in the analysis of the expression amount of β-galactosidase in each clone that while 16% exhibited the activity of 100 pg/$10^6$ cells/2 days or more in the CYH resistant clones, only 2% exhibited the equivalent expression amounts in the G418 resistant clone. Furthermore, it has been also found that some clones in the CYH resistant clones exhibited an activity exceeding 1000 pg/$10^6$ cells/2 days and the high expression strain can be also acquired efficiently in the cell lines into which lacZ has been stably transferred in the case of selection based on the resistance to CYH (FIG. 9).

Example 8

Measurement of Cell Growth Rate

The CYH resistant clones and the G418 resistant clones were compared on the growth rates under the conditions of the presence and absence of a drug. 15 clones were randomly selected from each of the CYH resistant clones and G418 resistant clones into which the SEAP gene has been transfected stably, and subcultured in a selective medium (containing 3 mg/ml of CYH or 1 mg/ml of G418) and in a non-selective medium, respectively. Specifically, each of the clones was seeded on 4–5 culturing dishes having a diameter of 10 cm at a density of $5\times10^5$ of cells, and the cells of one of the dishes was removed every day for counting the number of cells. Counting of cells in the suspension was carried out with a hemocytometer, a WST-1 cell proliferation reagent (Boehringer Mannheim, 1-644-807), or FACS. In the estimation with FACS, the cells suspended in PBS (−) supplemented with 2% FCS were stained with fluorescein diacetate (Wako Pure Chemical Industries, Ltd., 067-03311) in living cells and with propidium iodide (PI; Pharmingen, 66211E) in dead cells and subjected to FACS analysis to count the cells having green signals. According to the above described operations, a growth curve for 4–5 days was made and a growth per certain period of time was calculated on each of the clones.

The growth rate (g) of the drug resistant clone thus obtained was calculated according to the following equation 3 with $N_0$ as the number of cells at early stage, N as the number of cells at the end of culturing, and t as the culturing days.

$g=(\ln N - \ln N_0)/t$ (Equation 3):

The number of generation (x) was calculated according to the following equation 4.

$x=(\log_{10} N - \log_{10} N_0)/\log_{10} 2$ (Equation 4):

The doubling time was calculated by dividing the culturing time of the cells by the number of generation.

It has been confirmed in the growth curve that either of the CYH resistant clone and the G418 resistant clone tends to grow rapidly in the non-selective medium while to grow slowly in the selective medium, but no large differences were observed between marker genes and drugs (FIG. 10). For the purpose of further analysis of this point, each of the CYH resistant clones and the G418 resistant clones were seeded on a dish having a diameter of 10 cm at a density of $5\times10^5$ of cells and cultured for 3 days. The number of generation was calculated by counting the cells after the end of culturing, and an average doubling time per generation was calculated from the culturing time. In addition, the average doubling time of each of the clones in the selective medium and the non-selective medium was calculated by repeating the subculture several times. It has been found in the comparison of the average values of the average doubling times on 15 CYH resistant clones and 15 G418 resistant clones, respectively, in the selective medium and the non-selective medium that the average doubling time in the selective medium containing drugs is longer as compared to the one in the non-selective medium (FIG. 11). Also, no significant differences were observed in the average doubling times under the selective condition between two types of drug resistant clones and the non-selective condition, and thus it was believed that no difference of growth was present due to the kinds of the selective marker genes. In addition, the average doubling time was also calculated on non-transformed CHO cells, but it has been found slightly shorter than the one on the transformed cells.

It is concluded from these examinations that the effects of the marker gene of the present invention on the growth of the cells are equivalent to those of the widely used marker genes.

Example 9

Stability of Transduced Gene

As for the CYH resistant and G418 resistant clones into which the SEAP gene has been transduced, each of 6 clones in which SEAP is highly expressed was seeded on a dish having a diameter of 10 cm at a density of $5\times10^5$ of cells and cultured in a non-selective medium for 4 days. After culturing, the cells were recovered, counted with FACS according to the method described in Example 8, and seeded again on a dish having a diameter of 10 cm at a density of $5\times10^5$ of cells. The supernatant of the culture was subjected to SEAP assay. The sub-culturing operation was repeated in 8 or 9 times, and the SEAP expressions at each period (except the first subculture of the G418 resistant stain) was measured to check the stability of the transferred gene.

The SEAP expression in the CYH resistant clones was higher by a large margin than those of the G418 resistant stains, and such trend didn't vary with repeated sub-cultures in the non-selective medium (FIG. 12). Some of the clones in which SEAP is expressed highly among the CYH resistant clones decreased the amount of expression, but the amount of expression even after 8 cycles of subculture in the non-selective medium remained in a higher level than that of the SEAP expressions in the second sub-culture of the G418 resistant SEAP high expression clones. It has been found from these results that the gene inserted in chromosome is stable in the CHO cells in which a foreign gene has been transduced stably by the novel CYH resistant marker. It has been thus confirmed that the marker gene of L36a-CYH$^R$ is more useful than the marker gene of the widely used neo gene.

Example 10

Analysis of Copy Number of Transduced Foreign Gene

Among the SEAP gene transduced clones, 8 G418 resistant clones and 12 CYH resistant clones were subjected to the analysis of the number of copies of the SEAP gene by quantitative PCR. The genome DNA of the CHO cells was prepared with Wizard genomic DNA Purification kit (Promega, A1120). The concentration of the genome DNA prepared was measured quantitatively by measuring the absorbance at 260 nm. In addition, it was confirmed by electrophoresis with 1% agarose gel that no degradation was observed in DNA, and then the DNA was used as a template of quantitative PCR.

Quantitative PCR was carried out with The Lightcycler FastStart DNA Master SYBR Green (Roche Molecular Biochemicals, 3-003-230) in 45 cycles under the condition of 15 seconds at 95° C., 5 seconds at 57° C., and 10 seconds at 72° C. per cycle. The primer used was the SEAP forward (5'-GGT TAC CAC TCC CAC TGA CTT CC-3', SEQ ID NO: 9) and SEAP reverse (5'-GCA ACT TCC AGA CCA TTG GC-3', SEQ ID NO: 10). In order to standardize the results obtained by quantitative PCR with SEAP primer, PCR was carried out in the same manner as above with the forward primer (5'-ATG GGT CAG AAG GAT TCC TA-3') (SEQ ID NO: 16) and the reverse primer (5'-TCC ATG TCG TCC CAG TT-3') (SEQ ID NO:17) for β-actin which is attached to the Sentrnel Molecular Beacon b-Actin Detection kit (Straragene, 200570). PCR was carried out on the template DNA of each of the clones with two combinations of the primers. Relating to the amounts of the PCR reaction products of the SEAP gene and the β-actin gene, the relative values between clones were calculated on the basis of 1 as each of the minimal values. In addition, the relative value of the PCR product obtained with the SEAP primer in relation to the DNA of each clone was divided with the relative value of the PCR product obtained with the β-actin primer, which was regarded as the relative SEAP gene copies per amount of the unit genome DNA of each clone. The relationship between the relative SEAP gene copies of each clone and the SEAP expressions in the clone is illustrated graphically in FIG. 13, but no correlation was observed between the gene copies and the SEAP expressions. It has been possibly considered from the results that the high expression of a gene recognized frequently in the CYH resistant stain is the complicated effect of not only copies, but also the position of a foreign gene DNA inserted into chromosome and the other factors.

INDUSTRIAL APPLICABILITY

According to the present invention, in particular, recombinant cells in which the desired protein is expressed in a high level are selected in a high frequency by selecting a transfected cell with a vector containing a novel selective marker gene (protein synthesis inhibitor resistant gene, typically cycloheximide resistant gene). It is possible to decrease the number of transfected cells that require screening for the purpose of selecting a high expression strain by using the vector.

In addition, the above described vector which can efficiently acquire cells in which a foreign gene is highly expressed in a short time is expected to make a large contribution to the analysis of functions of a protein having unknown functions coded for the gene and to the development of the production system of recombinant proteins which can be used as pharmaceuticals.

What is claimed is:

1. A process for selecting an animal cell strain resistant to a protein synthesis inhibitor, comprising:

introducing an expression vector containing (A) a protein synthesis inhibitor resistance gene which is capable of imparting cycloheximide resistance to animal cells sensitive to cycloheximide and which encodes the amino acid sequence comprising SEQ ID NO: 11 or a sequence at least 99% homologous thereto, wherein said amino acid sequence contains an amino acid other than proline at the position corresponding to position 54 of SEQ ID NO: 11 and (B) a gene encoding a foreign protein in an expressible state, into animal cells sensitive to cycloheximide, culturing the cells with the protein synthesis inhibitor cycloheximide, to express the foreign protein, and selecting the animal cell strain that is resistant to cycloheximide.

2. A process according to claim 1, wherein the animal cell strain sensitive to cycloheximide is derived from a mammal.

3. A process according to claim 2, wherein the animal cell is a CHO cell from the ovary of a Chinese hamster.

4. A process according to claim 3, wherein the animal cell is a CHO cell lacking dihydrofolic acid reductase.

5. A process for producing a protein, characterized by culturing transformed animal cells containing the expression vector defined in claim 1 and collecting a foreign protein expressed by the cells.

6. A process according to claim 1, wherein the sequence at least 99% homologous encodes a ribosome protein L44, which has the amino acid sequence comprising SEQ ID NO:12.

* * * * *